United States Patent
Roy

(10) Patent No.: US 12,156,761 B1
(45) Date of Patent: Dec. 3, 2024

(54) BAYESIAN ANATOMICALLY-DRIVEN, ARTIFICIAL-INTELLIGENCE BASED INTRACARDIAC ECHOCARDIOGRAPHY OBJECT DETECTION AND PREDICTION

(71) Applicant: yoR Labs, Inc., Beaverton, OR (US)

(72) Inventor: Anshumali Roy, Beaverton, OR (US)

(73) Assignee: yoR Labs, Inc., Beaverton, OR (US)

( * ) Notice: Subject to any disclaimer, the term of this patent is extended or adjusted under 35 U.S.C. 154(b) by 0 days.

(21) Appl. No.: 18/642,683

(22) Filed: Apr. 22, 2024

Related U.S. Application Data

(60) Provisional application No. 63/561,650, filed on Mar. 5, 2024.

(51) Int. Cl.
*A61B 8/08* (2006.01)
*A61B 8/00* (2006.01)
(Continued)

(52) U.S. Cl.
CPC ............ *A61B 8/0883* (2013.01); *A61B 8/12* (2013.01); *A61B 8/463* (2013.01); *A61B 8/469* (2013.01);
(Continued)

(58) Field of Classification Search
CPC ............ G06F 18/24155; G06V 20/70; G06V 2201/031; G16H 50/20
See application file for complete search history.

(56) References Cited

U.S. PATENT DOCUMENTS 4,998,132 A   3/1991   Kurogane
5,364,351 A   11/1994  Heinzelman et al.
(Continued)

FOREIGN PATENT DOCUMENTS

AU   2018250516   11/2018
EP   2 818 115    12/2014
(Continued)

OTHER PUBLICATIONS

Bradley, Aug. 2008, Retrospective transmit beamformation: Acuson SC2000 volume imaging ultrasound system, Siemens Medical Solutions USA, Inc., whitepaper, 8 pp.
(Continued)

*Primary Examiner* — Peter Luong
(74) *Attorney, Agent, or Firm* — Knobbe, Martens, Olson & Bear, LLP

(57) ABSTRACT

The systems and methods perform Bayesian anatomically-driven, artificial-intelligence based intracardiac echocardiography object detection and prediction. The system proposes hypotheses for what features and objects are in view based on prior knowledge informed by previously acquired or generated models. During a cardiac interventional procedure, the system uses a per-frame object identification artificial intelligence (AI); the gathered data is analyzed within a Bayesian framework to create updated posterior prediction(s) of what feature(s) may be predicted (with a computed confidence level) to be in view and their respective location(s). Inferences that pass an accept/reject threshold for object identification and meet minimum threshold settings for temporal stability and spatial location are used to display labels and boundaries. The system predicts what features and objects are in-frame, where out-of-frame objects/features may be located, and how to navigate to them.

19 Claims, 20 Drawing Sheets

(51) Int. Cl.
  *A61B 8/12* (2006.01)
  *G06F 18/2415* (2023.01)
  *G06V 20/70* (2022.01)
  *G16H 50/20* (2018.01)
(52) U.S. Cl.
  CPC ...... *A61B 8/5261* (2013.01); *G06F 18/24155* (2023.01); *G06V 20/70* (2022.01); *G16H 50/20* (2018.01); *G06V 2201/031* (2022.01)

(56) References Cited

U.S. PATENT DOCUMENTS

| | | | |
|---|---|---|---|
| 5,617,371 | A | 4/1997 | Williams |
| 5,903,516 | A | 5/1999 | Greenleaf et al. |
| 5,908,389 | A | 6/1999 | Roundhill et al. |
| 6,031,529 | A | 2/2000 | Migos |
| 6,063,030 | A | 5/2000 | Vara et al. |
| 6,120,450 | A | 9/2000 | Li |
| 6,123,670 | A | 9/2000 | Mo |
| 6,132,374 | A | 10/2000 | Hossack et al. |
| 6,400,981 | B1 | 6/2002 | Govari |
| 6,607,489 | B2 | 8/2003 | Hoctor |
| 6,689,062 | B1 * | 2/2004 | Mesallum ......... A61B 18/1492 606/1 |
| 6,690,963 | B2 | 2/2004 | Ben Haim et al. |
| 6,908,434 | B1 | 6/2005 | Jenkins et al. |
| 7,090,639 | B2 | 8/2006 | Govari |
| 7,423,578 | B1 | 9/2008 | Tietjen |
| 7,604,601 | B2 | 10/2009 | Altmann et al. |
| 7,648,462 | B2 | 1/2010 | Jenkins et al. |
| 7,667,639 | B2 | 2/2010 | Cheng et al. |
| 7,682,358 | B2 | 3/2010 | Gullickson et al. |
| 7,750,849 | B2 | 7/2010 | Hjelmstad |
| 7,831,076 | B2 | 11/2010 | Altmann et al. |
| 7,860,553 | B2 | 12/2010 | Govari et al. |
| 7,918,793 | B2 | 4/2011 | Altmann et al. |
| 7,996,060 | B2 | 8/2011 | Trofimov et al. |
| 8,075,486 | B2 | 12/2011 | Tal |
| 8,285,364 | B2 | 10/2012 | Barbagli et al. |
| 8,390,438 | B2 | 3/2013 | Olson et al. |
| 8,449,467 | B2 | 5/2013 | Wilser et al. |
| 8,517,946 | B2 | 8/2013 | Kim |
| 8,676,290 | B2 | 3/2014 | Tegg |
| 8,690,871 | B2 | 4/2014 | Partlett et al. |
| 8,702,612 | B2 | 4/2014 | Hendriks et al. |
| 8,989,842 | B2 | 3/2015 | Li et al. |
| 9,030,354 | B2 | 5/2015 | Natarajan |
| 9,055,883 | B2 | 6/2015 | Tgavalekos et al. |
| 9,095,682 | B2 | 8/2015 | Romoscanu |
| 9,132,913 | B1 | 9/2015 | Shapiro et al. |
| 9,179,890 | B2 | 11/2015 | Ionasec et al. |
| 9,211,160 | B2 | 12/2015 | Pivotto et al. |
| 9,261,595 | B2 | 2/2016 | Garbini et al. |
| 9,323,445 | B2 | 4/2016 | Kritt et al. |
| 9,342,156 | B2 | 5/2016 | Huh |
| 9,922,554 | B2 | 3/2018 | Mikuni et al. |
| 9,931,487 | B2 | 4/2018 | Quinn et al. |
| 9,986,969 | B2 | 6/2018 | Call et al. |
| 10,183,149 | B2 | 1/2019 | Tegg et al. |
| 10,206,652 | B2 | 2/2019 | Deno et al. |
| 10,368,951 | B2 | 8/2019 | Moll et al. |
| 10,401,492 | B2 | 9/2019 | Brooks |
| 10,405,830 | B2 | 9/2019 | Garbini et al. |
| 10,463,439 | B2 | 11/2019 | Joseph et al. |
| 10,499,882 | B2 | 12/2019 | Hunter et al. |
| 10,537,307 | B2 | 1/2020 | Yang |
| 10,555,780 | B2 | 2/2020 | Tanner et al. |
| 10,624,612 | B2 | 4/2020 | Sumi |
| 11,255,964 | B2 | 2/2022 | Brooks |
| 11,344,281 | B2 | 5/2022 | Morisse et al. |
| 11,547,386 | B1 | 1/2023 | Roy et al. |
| 11,704,142 | B2 | 7/2023 | Morrise |
| 11,751,850 | B2 | 9/2023 | Morrise |
| 11,832,991 | B2 | 12/2023 | Morrise |
| 11,892,542 | B1 | 2/2024 | Brooks |
| 11,998,391 | B1 | 6/2024 | Roy et al. |
| 2002/0173721 | A1 | 11/2002 | Grunwald |
| 2002/0173722 | A1 | 11/2002 | Hoctor et al. |
| 2003/0007598 | A1 | 1/2003 | Wang et al. |
| 2003/0055334 | A1 | 3/2003 | Steinbacher et al. |
| 2003/0055337 | A1 | 3/2003 | Lin |
| 2004/0102700 | A1 | 5/2004 | Asafusa |
| 2005/0288588 | A1 | 12/2005 | Weber et al. |
| 2006/0173663 | A1 * | 8/2006 | Langheier ......... G16H 50/20 703/11 |
| 2007/0027733 | A1 | 2/2007 | Balle |
| 2007/0038088 | A1 | 2/2007 | Rich |
| 2007/0174772 | A1 | 7/2007 | Gorman |
| 2007/0200760 | A1 | 8/2007 | Hjelmstad |
| 2007/0239001 | A1 | 10/2007 | Mehi et al. |
| 2007/0259158 | A1 | 11/2007 | Friedman et al. |
| 2008/0012753 | A1 | 1/2008 | Cheng |
| 2008/0114239 | A1 | 5/2008 | Randall et al. |
| 2008/0146940 | A1 | 6/2008 | Jenkins et al. |
| 2008/0215046 | A1 | 9/2008 | Messing et al. |
| 2008/0306385 | A1 | 12/2008 | Jago |
| 2009/0043206 | A1 | 2/2009 | Towfiq et al. |
| 2009/0118620 | A1 * | 5/2009 | Tgavalekos ......... A61B 8/4254 600/463 |
| 2009/0171275 | A1 | 7/2009 | Ostrovsky et al. |
| 2009/0250729 | A1 | 10/2009 | Lemmerhirt |
| 2009/0271704 | A1 | 10/2009 | Cohen |
| 2010/0030076 | A1 | 2/2010 | Vortman et al. |
| 2010/0081938 | A1 | 4/2010 | Kato |
| 2010/0146431 | A1 | 6/2010 | Raji et al. |
| 2010/0160784 | A1 | 6/2010 | Poland |
| 2010/0168580 | A1 | 7/2010 | Thiele |
| 2010/0234831 | A1 | 9/2010 | Hinman et al. |
| 2010/0251823 | A1 | 10/2010 | Adachi |
| 2011/0077524 | A1 | 3/2011 | Oshiki et al. |
| 2011/0137132 | A1 | 6/2011 | Gustafson |
| 2011/0208052 | A1 | 8/2011 | Entrekin |
| 2011/0225114 | A1 * | 9/2011 | Gotthardt ......... G16H 10/20 706/50 |
| 2012/0075208 | A1 | 3/2012 | Tamiya et al. |
| 2012/0157851 | A1 | 6/2012 | Zwirn |
| 2012/0254747 | A1 | 10/2012 | Bocirnea |
| 2013/0015975 | A1 | 1/2013 | Huennekens et al. |
| 2013/0035596 | A1 * | 2/2013 | Ionasec ......... G06T 7/344 600/450 |
| 2013/0120296 | A1 | 5/2013 | Merritt et al. |
| 2013/0227052 | A1 | 8/2013 | Wenzel |
| 2013/0234891 | A1 | 9/2013 | Natarajan et al. |
| 2013/0238990 | A1 | 9/2013 | Ubillos et al. |
| 2013/0253317 | A1 | 9/2013 | Gauthier |
| 2013/0274712 | A1 | 10/2013 | Schecter et al. |
| 2013/0310690 | A1 | 11/2013 | Chang |
| 2014/0035916 | A1 | 2/2014 | Murphy |
| 2014/0046188 | A1 | 2/2014 | Yen et al. |
| 2014/0058266 | A1 | 2/2014 | Call et al. |
| 2014/0059486 | A1 | 2/2014 | Sasaki et al. |
| 2014/0087342 | A1 | 3/2014 | Campanatti, Jr. |
| 2014/0164965 | A1 | 6/2014 | Lee et al. |
| 2014/0189560 | A1 | 7/2014 | Caspi |
| 2014/0219059 | A1 | 8/2014 | Younghouse |
| 2014/0336573 | A1 | 11/2014 | Yu et al. |
| 2015/0019488 | A1 | 1/2015 | Higginson et al. |
| 2015/0065877 | A1 | 3/2015 | Orderud |
| 2015/0082251 | A1 | 3/2015 | Lam |
| 2015/0293223 | A1 | 10/2015 | Park et al. |
| 2016/0054901 | A1 | 2/2016 | Yang et al. |
| 2016/0095650 | A1 | 4/2016 | Greifenender et al. |
| 2016/0157824 | A1 | 6/2016 | Park et al. |
| 2016/0161589 | A1 | 6/2016 | Benattar |
| 2016/0161594 | A1 | 6/2016 | Benattar |
| 2016/0161595 | A1 | 6/2016 | Benattar |
| 2016/0165338 | A1 | 6/2016 | Benattar |
| 2016/0165341 | A1 | 6/2016 | Benattar |
| 2016/0338676 | A1 | 11/2016 | Berger et al. |
| 2017/0072167 | A1 | 3/2017 | Weitzner et al. |
| 2017/0090571 | A1 | 3/2017 | Bjaerum |
| 2017/0153801 | A1 | 6/2017 | Kim et al. |
| 2017/0266413 | A1 | 9/2017 | Khuu et al. |
| 2017/0307755 | A1 | 10/2017 | Brooks |

(56) References Cited

U.S. PATENT DOCUMENTS

| | | |
|---|---|---|
| 2017/0326337 A1 | 11/2017 | Romoscanu et al. |
| 2017/0343655 A1 | 11/2017 | Solek et al. |
| 2017/0343668 A1 | 11/2017 | Brooks et al. |
| 2018/0000449 A1 | 1/2018 | Moore et al. |
| 2018/0000453 A1 | 1/2018 | Hunter et al. |
| 2018/0003811 A1 | 1/2018 | Pellegretti |
| 2018/0055483 A1 | 3/2018 | Hunter |
| 2018/0064415 A1 | 3/2018 | Zhai et al. |
| 2018/0361145 A1 | 12/2018 | Mahapatra et al. |
| 2019/0201110 A1 | 7/2019 | Kuenen |
| 2019/0245310 A1 | 8/2019 | Medina et al. |
| 2019/0261953 A1 | 8/2019 | Honjo et al. |
| 2019/0307427 A1 | 10/2019 | Levy et al. |
| 2019/0353975 A1 | 11/2019 | DiDomenico |
| 2020/0000430 A1 | 1/2020 | Chamberlain |
| 2020/0046321 A1 | 2/2020 | Duda |
| 2020/0060646 A1 | 2/2020 | Lindenroth et al. |
| 2020/0170662 A1 | 6/2020 | Vardi |
| 2020/0178928 A1 | 6/2020 | Park et al. |
| 2020/0183004 A1 | 6/2020 | Gong et al. |
| 2020/0205783 A1 | 7/2020 | Shiran |
| 2020/0268351 A1 | 8/2020 | Chiang |
| 2020/0281565 A1 | 9/2020 | Yee et al. |
| 2020/0297318 A1 | 9/2020 | Srinivasa et al. |
| 2020/0315592 A1 | 10/2020 | Soleimani et al. |
| 2020/0330076 A1 | 10/2020 | Weber |
| 2021/0007710 A1 | 1/2021 | Douglas |
| 2021/0022716 A1 | 1/2021 | Kerby |
| 2021/0030394 A1 | 2/2021 | Caswell et al. |
| 2021/0038334 A1 | 2/2021 | Hsu et al. |
| 2021/0125503 A1 | 4/2021 | Henry et al. |
| 2021/0177379 A1 | 6/2021 | Kolen et al. |
| 2021/0196237 A1 | 7/2021 | Bellamkonda |
| 2021/0338208 A1 | 11/2021 | Nguyen et al. |
| 2021/0401400 A1 | 12/2021 | Sheehan et al. |
| 2021/0401508 A1 | 12/2021 | Zhao |
| 2022/0061811 A1 | 3/2022 | Terleski |
| 2022/0061906 A1 | 3/2022 | Gommeren et al. |
| 2022/0401081 A1 | 12/2022 | Sheeran et al. |
| 2023/0026942 A1* | 1/2023 | Meral ............... A61B 8/465 |
| 2023/0059122 A1 | 2/2023 | Pellegrino |

FOREIGN PATENT DOCUMENTS

| | | |
|---|---|---|
| EP | 2 842 497 | 3/2015 |
| EP | 2 288 284 | 5/2016 |
| EP | 3 275 478 | 1/2018 |
| EP | 2 707 076 | 11/2018 |
| EP | 3 050 214 | 3/2019 |
| EP | 3 371 624 | 6/2019 |
| EP | 2 632 318 | 11/2019 |
| EP | 3 518 777 | 3/2021 |
| WO | WO 02/13682 | 2/2002 |
| WO | WO 09/079695 | 7/2009 |
| WO | WO 10/051587 | 5/2010 |
| WO | WO 12/088535 | 6/2012 |
| WO | WO 17/185097 | 10/2017 |
| WO | WO 20/049012 | 3/2020 |
| WO | WO 20/252416 | 12/2020 |

OTHER PUBLICATIONS

Lin et al., Jun. 2010, A motion compounding technique for speckle reduction in ultrasound images, Journal of digital imaging 23(3):246-257.

Pandian et al., Jun. 18, 1992, Intravascular ultrasound and intracardiac echocardiography: concepts for the future, American Journal of Cardiology, 69(20):H6-H17.

* cited by examiner

BAYESIAN ANATOMICALLY-DRIVEN, ARTIFICIAL-INTELLIGENCE BASED INTRACARDIAC ECHOCARDIOGRAPHY OBJECT DETECTION AND PREDICTION

BACKGROUND

Object and feature detection in single images and video (sequence of images known as frames) has been an evolving field over the past several decades. Convolutional neural networks (CNNs) are commonly used for object and feature detection in static images. During the last ten years there have been other advances and approaches that range from improved CNNs (for example, a residual network or ResNet) to more recent applications of transformer networks to model attention to various parts of an image while accelerating computational wall-clock time via intensive parallel processing. Additionally, single image and object recognition systems have also attempted to model training parameter variability, such as Bayesian Neural Networks (BNNs), but these existing applications have been directed towards variability modeling within the same image.

Electroanatomic mapping (EAM) is a method of creating a three-dimensional model of the human heart during clinical cardiac electrophysiology procedures. Existing EAM systems can use external magnets to locate catheters in vivo and create a three-dimensional model of the human heart.

SUMMARY

The systems, methods, and devices described herein each have several aspects, no single one of which is solely responsible for its desirable attributes. Without limiting the scope of this disclosure, several non-limiting features will now be discussed briefly.

In some aspects, the techniques described herein relate to a system including: an intracardiac echocardiography catheter device; a non-transitory data storage medium; and one or more computer hardware processors in communication with the non-transitory data storage medium, wherein the one or more computer hardware processors are configured to execute computer-executable instructions to at least: receive a set of prior distributions; receive a first intracardiac echocardiography image of a subject based at least in part on data from the intracardiac echocardiography catheter device; receive, from an object detector, (i) a first predicted feature or object identified in the first intracardiac echocardiography image and (ii) a first location of the first predicted feature or object relative to the first intracardiac echocardiography image; determine a set of posterior predictions from at least (i) a Bayesian method, (ii) the set of prior distributions, (iii) the first intracardiac echocardiography image, (iv) the first predicted feature or object, and (v) the first location of the first predicted feature or object, wherein a first posterior prediction from the set of posterior predictions indicates a first probability distribution associated with the first predicted feature or object; determine that the first probability distribution satisfies a first threshold; and display, in a graphical user interface, (i) a first label for the first predicted feature or object associated with the first location and (ii) the first intracardiac echocardiography image.

In some aspects, the techniques described herein relate to a system, wherein the set of prior distributions includes a first prior distribution, wherein the one or more computer hardware processors is configured to execute further computer-executable instructions to at least: determine the first prior distribution from at least one of a synthetic volumetric model of a heart, cardiac computed tomography volumetric data of another subject, or cardiac computed tomography volumetric data of the subject.

In some aspects, the techniques described herein relate to a system, wherein the one or more computer hardware processors is configured to execute further computer-executable instructions to at least: receive an anatomical model, wherein the set of posterior predictions is further determined from at least the anatomical model, and wherein a second posterior prediction from the set of posterior predictions indicates a second probability distribution associated with (i) a second predicted feature or object not identified in the first intracardiac echocardiography image and (ii) a second location of the second predicted feature or object relative to the first intracardiac echocardiography image; determine that the second probability distribution satisfies a second threshold; and display, in the graphical user interface, a second label for the second predicted feature or object associated with the second location, wherein the second location is outside of the first intracardiac echocardiography image.

In some aspects, the techniques described herein relate to a system, wherein the one or more computer hardware processors is configured to execute further computer-executable instructions to at least: assign a first location and a first orientation to a device object in an anatomical model; receive, via the graphical user interface, user input that indicates a target location within the anatomical model; determine a navigational element from the first location, the first orientation, and the target location; and display, in a graphical user interface, the navigational element and a second intracardiac echocardiography image.

In some aspects, the techniques described herein relate to a system, wherein the one or more computer hardware processors is configured to execute further computer-executable instructions to at least: receive a second set of prior distributions; receive a second intracardiac echocardiography image based at least in part on second data from the intracardiac echocardiography catheter device; receive, from the object detector, (i) a second predicted feature or object identified in the second intracardiac echocardiography image and (ii) a second location of the second predicted feature or object relative to the second intracardiac echocardiography image; determine a second set of posterior predictions from at least (i) the Bayesian method, (ii) the second set of prior distributions, (iii) the second intracardiac echocardiography image, (iv) the second predicted feature or object, and (v) the second location of the first predicted feature or object, wherein a second posterior prediction from the second set of posterior predictions indicates a second probability distribution associated with the second predicted feature or object; determine that the second probability distribution fails to satisfy a second threshold; and initiate a reset state, wherein initiating the reset state includes resetting a set of prior distributions.

In some aspects, the techniques described herein relate to a system, wherein the one or more computer hardware processors is configured to execute further computer-executable instructions to at least: determine a Markov chain including a first state corresponding to the first predicted feature or object and a second state corresponding to an out-of-frame predicted feature or object, wherein determining the set of posterior predictions further includes feeding the Markov chain into the Bayesian method.

In some aspects, the techniques described herein relate to a system including: an intracardiac echocardiography catheter device; a non-transitory data storage medium; and one or more computer hardware processors in communication with the non-transitory data storage medium, wherein the one or more computer hardware processors are configured to execute computer-executable instructions to at least: receive a first set of prior distributions; receive a first intracardiac echocardiography image of a subject based at least in part on first data from the intracardiac echocardiography catheter device; receive, from an object detector, (i) a first predicted feature or object identified in the first intracardiac echocardiography image and (ii) a first location of the first predicted feature or object relative to the first intracardiac echocardiography image; determine a first set of posterior predictions from at least (i) a Bayesian method, (ii) the first set of prior distributions, (iii) the first intracardiac echocardiography image, (iv) the first predicted feature or object, and (v) the first location of the first predicted feature or object, wherein a first posterior prediction from the first set of posterior predictions indicates a first probability distribution associated with the first predicted feature or object; determine that the first probability distribution fails to satisfy a first threshold; receive a second set of prior distributions; receive a second intracardiac echocardiography image of the subject based at least in part on second data from the intracardiac echocardiography catheter device; receive, from the object detector, (i) a second predicted feature or object identified in the second intracardiac echocardiography image and (ii) a second location of the second predicted feature or object relative to the second intracardiac echocardiography image; determine a second set of posterior predictions from at least (i) the Bayesian method, (ii) the second set of prior distributions, (iii) the second intracardiac echocardiography image, (iv) the second predicted feature or object, and (v) the second location of the first predicted feature or object, wherein a second posterior prediction from the second set of posterior predictions indicates a second probability distribution associated with the second predicted feature or object; determine that the second probability distribution satisfies a second threshold; and display, in a graphical user interface, (i) a label for the second predicted feature or object associated with the second location and (ii) the second intracardiac echocardiography image.

In some aspects, the techniques described herein relate to a system, wherein the one or more computer hardware processors is configured to execute further computer-executable instructions to at least: determine a Markov chain including a first state corresponding to the first predicted feature or object and a second state, wherein determining the second set of posterior predictions further includes feeding the Markov chain into the Bayesian method.

In some aspects, the techniques described herein relate to a system, wherein the one or more computer hardware processors is configured to execute further computer-executable instructions to at least: receive vitals data for the subject; and determine, from the vitals data, a cardiac cycle, wherein the second state corresponds to the cardiac cycle.

In some aspects, the techniques described herein relate to a system, wherein the one or more computer hardware processors is configured to execute further computer-executable instructions to at least: receive degrees of freedom sensor data associated with the intracardiac echocardiography catheter device; and determine an orientation from the degrees of freedom sensor data, wherein the second state corresponds to the orientation.

In some aspects, the techniques described herein relate to a system, wherein determining the second set of posterior predictions further includes applying a Markov chain Monte Carlo method.

In some aspects, the techniques described herein relate to a system, wherein the one or more computer hardware processors is configured to execute further computer-executable instructions to at least: receive an anatomical model, wherein the second set of posterior predictions is further determined from at least the anatomical model, and wherein a third posterior prediction from the second set of posterior predictions indicates a third probability distribution associated with (i) a third predicted feature or object not identified in the second intracardiac echocardiography image and (ii) a third location of the third predicted feature or object relative to the second intracardiac echocardiography image; determine that the third probability distribution satisfies a third threshold; and display, in the graphical user interface, a third label for the third predicted feature or object associated with the third location, wherein the third location is outside of the second intracardiac echocardiography image.

In some aspects, the techniques described herein relate to a system, wherein the one or more computer hardware processors is configured to execute further computer-executable instructions to at least: assign a first location and a first orientation to a device object in an anatomical model; receive, via the graphical user interface, user input that indicates a target location within the anatomical model; determine a navigational element from the first location, the first orientation, and the target location; and display, in a graphical user interface, the navigational element and a third intracardiac echocardiography image.

In some aspects, the techniques described herein relate to a method including: receiving a set of prior distributions; receiving a first intracardiac echocardiography image of a subject based at least in part on data from an intracardiac echocardiography catheter device; receiving, from an object detector, (i) a first predicted feature or object identified in the first intracardiac echocardiography image and (ii) a first location of the first predicted feature or object relative to the first intracardiac echocardiography image; determining a set of posterior predictions from at least (i) a Bayesian method, (ii) the set of prior distributions, (iii) the first intracardiac echocardiography image, (iv) the first predicted feature or object, and (v) the first location of the first predicted feature or object, wherein a first posterior prediction from the set of posterior predictions indicates a first probability distribution associated with the first predicted feature or object; determining that the first probability distribution satisfies a first threshold; and displaying, in a graphical user interface, (i) a first label for the first predicted feature or object associated with the first location and (ii) the first intracardiac echocardiography image.

In some aspects, the techniques described herein relate to a method, further including: receiving an anatomical model, wherein the set of posterior predictions is further determined from at least the anatomical model, and wherein a second posterior prediction from the set of posterior predictions indicates a second probability distribution associated with (i) a second predicted feature or object not identified in the first intracardiac echocardiography image and (ii) a second location of the second predicted feature or object relative to the first intracardiac echocardiography image; determining that the second probability distribution satisfies a second threshold; and displaying, in the graphical user interface, a second label for the second predicted feature or object associated with the second location, wherein the second location is outside of the first intracardiac echocardiography image.

In some aspects, the techniques described herein relate to a method, further including: assigning a first location and a first orientation to a device object in an anatomical model;

receiving, via the graphical user interface, user input that indicates a target location within the anatomical model; determining a navigational element from the first location, the first orientation, and the target location; and displaying, in a graphical user interface, the navigational element and a second intracardiac echocardiography image.

In some aspects, the techniques described herein relate to a method, further including: receiving a second set of prior distributions; receiving a second intracardiac echocardiography image based at least in part on second data from the intracardiac echocardiography catheter device; receiving, from the object detector, (i) a second predicted feature or object identified in the second intracardiac echocardiography image and (ii) a second location of the second predicted feature or object relative to the second intracardiac echocardiography image; determining a second set of posterior predictions from at least (i) the Bayesian method, (ii) the second set of prior distributions, (iii) the second intracardiac echocardiography image, (iv) the second predicted feature or object, and (v) the second location of the first predicted feature or object, wherein a second posterior prediction from the second set of posterior predictions indicates a second probability distribution associated with the second predicted feature or object; determining that the second probability distribution fails to satisfy a first threshold; and initiating a reset state, wherein initiating the reset state includes resetting a set of prior distributions.

In some aspects, the techniques described herein relate to a method, further including: determining a Markov chain including a first state corresponding to the first predicted feature or object and a second state corresponding to an out-of-frame predicted feature or object, wherein determining the set of posterior predictions further includes feeding the Markov chain into the Bayesian method.

In some aspects, the techniques described herein relate to a method, further including: receiving vitals data; and determining, from the vitals data, a cardiac cycle, wherein the second state corresponds to the cardiac cycle.

In some aspects, the techniques described herein relate to a method, further including: receiving degrees of freedom sensor data associated with the intracardiac echocardiography catheter device; and determining an orientation from the degrees of freedom sensor data, wherein the second state corresponds to the orientation.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

BRIEF DESCRIPTION OF THE DRAWINGS

These and other features, aspects, and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters can denote corresponding features throughout similar embodiments. The following is a brief description of each of the drawings.

DETAILED DESCRIPTION

Figure 1:
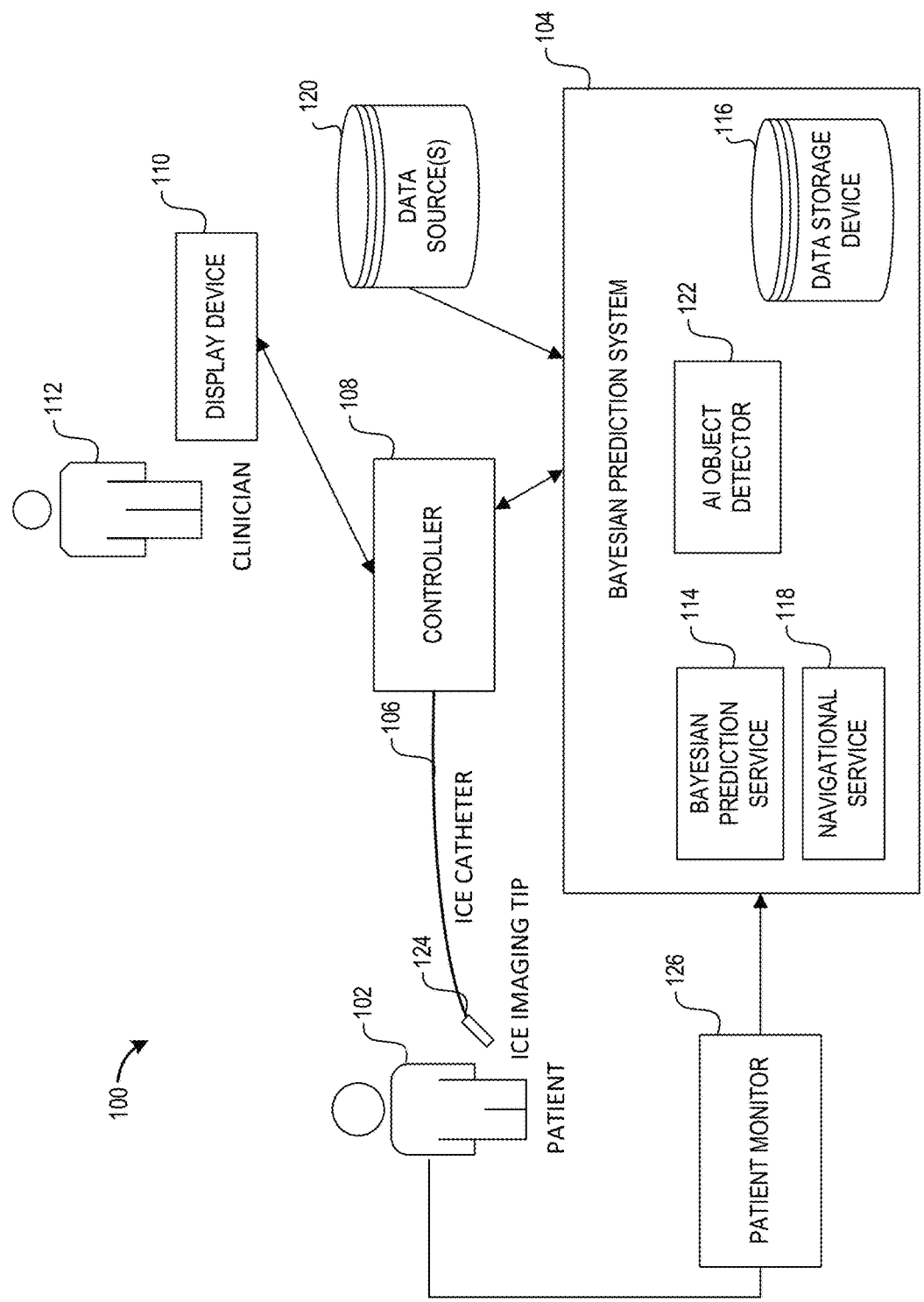
FIG. 1 is a schematic block diagram depicting an example of an environment including a Bayesian prediction system that can perform intracardiac echocardiography objection detection and prediction.

Intracardiac echocardiography (ICE) uses sound waves to produce images of the heart. During intracardiac echocardiography, a narrow catheter with an ultrasound sensor is passed into the heart where images of the heart can be captured. Intracardiac echocardiography has become an integral part of a variety of percutaneous interventional and electrophysiology procedures. However, a clinician (such as a cardiologist) performing such procedures can have difficulty localizing a catheter within the heart. For example, if a clinician sets a catheter handle down, then the clinician may easily lose their position in the heart. In such cases, the clinician often returns the catheter back to a "home" location or view, thereby adding to the procedure time. Therefore, clinicians can benefit from a system that can, substantially in real time, (1) perform object/feature detection and label objects within a heart, (2) predict future objects/features that could be seen as the clinician moves the catheter within the heart, and/or (3) provide directions to a clinician on how to get to other locations within the heart. As described above, EAM systems can locate a catheter within the heart; however, such existing systems lack the ability to (1) perform object detection and label objects/features within a heart, (2) predict future objects/features that could be seen as the clinician moves the catheter within the heart, and/or (3) provide directions to a clinician on how to get to other locations within the heart.

The existing object and feature detection methods described above struggle in dynamically changing environments, such as intracardiac imaging. Detecting objects and features during intracardiac imaging is technically challenging due to a very large number of system imaging control options, for example, imaging angle, imaging depth, focal depth and number of focal points, imaging aperture and other image quality settings, and the cardiac environment itself which consists of chamber deformations during systolic and diastolic phases, turbulent fluid flow, large variation in size, abnormalities, and/or wall or valve dynamics specific to particular subjects.

Generally described, aspects of the present disclosure are directed to Bayesian systems and methods that can detect/predict objects and features during intracardiac echocardiography based on prior knowledge. The systems and methods can propose hypotheses for what features and objects are in view based on prior knowledge informed by previously acquired or generated models. The models can include, but are not limited to, CAD-models and/or models acquired via computed tomography (CT) studies on one or multitude of patients including the particular subject and labeled appropriately (which can also be done by the systems and methods described herein under some limited human supervision). During a cardiac interventional procedure, the system can use a per-frame object identification artificial intelligence (AI) system as a data gathering system. The gathered data can then be analyzed within a Bayesian framework to create updated posterior prediction(s) of what feature(s) may be predicted (with a computed confidence level) to be in view and their respective location(s). Inferences that pass an accept/reject threshold for object identification and meet minimum threshold settings for temporal stability and spatial location can then be used to display, substantially in real-time and with respect to intracardiac echocardiography images, labels and boundaries of spatial features (e.g. cardiac chambers, valves, walls) or other interventional devices, such as, but not limited to, catheters, wires, or implantable devices. By utilizing a Bayesian supervisor on an AI image recognition system and tying it back into an anatomical model, the systems and methods described herein can predict what features and objects are in-frame, where out-of-frame objects/features may be located, and how to navigate to them.

Turning to FIG. 1, an illustrative environment 100 is shown. The environment 100 can include a Bayesian prediction system 104, a controller 108, an ICE catheter 106, a patient monitor 126, a display device 110, and data source(s) 120. The Bayesian prediction system 104 can include a Bayesian prediction service 114, a navigational service 118, an AI object detector 122, and a data storage device 116. During a cardiac interventional procedure, intracardiac images associated with the patient 102 can be captured via the ICE catheter 106 and a controller 108. The intracardiac images associated with the patient 102 can be presented in a graphical user interface via the display device 110. The display device 110 can be a part of an integrated data display system (IDDS) within an interventional cardiology suite.

A clinician 112 can use the graphical user interface to control the ICE catheter 106 via the controller 108. The ICE catheter 106 can include an ICE imaging tip 124 on the distal end of the catheter 106. In some embodiments, the controller 108 can include one or more motors, electrical connections, power delivery circuitry, an interface, signal transmit and receipt circuitry, and/or components that allow the controller 108 to steer and/or rotate the ICE catheter 106, communicate signals to the ICE imaging tip 124, and/or receive signals from the ICE imaging tip 124. The clinician 112 can control the operation of the ICE catheter 106, such as, but not limited to, steering, imaging, and/or ablation. The ICE catheter 106 and the controller 108 can be collectively referred to as an intracardiac echocardiography catheter device.

In some embodiments, a patient monitor 126 can capture patient vitals data, such as, but not limited to electrocardiogramata. For example, external ECG electrodes can be placed on the patient's 102 chest. The patient monitor 126 can transmit vitals data to the Bayesian prediction system 104.

As described herein, before the procedure, the Bayesian prediction system 104 can process existing models to develop a Prior. The Bayesian prediction system 104 can receive the existing models from one or more data sources 120. The existing models can include, but are not limited to, a synthetic volumetric model of the heart, a volumetric image library of cardiac CT volumes, and/or CT data of the subject, each of which can be pre-labeled.

During the cardiac interventional procedure, the Bayesian prediction system 104 can receive intracardiac images (which can be referred to as "frames") associated with the patient 102. As described herein, the Bayesian prediction service 114 and the AI object detector 122 can receive the frames. The Bayesian prediction service 114 can receive additional data, such as, vitals data (which can include ECG or blood pressure data) and/or catheter-tip embedded multi-degrees of freedom (DOF) sensor data. The AI object detector 122 can detect objects/features; however, as described herein, corresponding object/feature labels may not be displayed until the detected objects satisfy a quality evaluation test. The Bayesian prediction service 114 can make Bayesian predictions (posterior predictions from priors) for each object/feature per-frame. If a likelihood (such as a confidence interval) does not satisfy a threshold, then the Bayesian prediction service 114 may not cause the object/feature to be displayed and may return to an earlier state (such as a reset) and/or may process new incoming images and/or additional data. In some embodiments, based on the predicted objects/features that satisfy a quality evaluation, the navigational service 118 can construct navigational guidance, such as by generating indicators that can be displayed to the clinician 112 in order to provide guidance assistance the clinician 112 during the procedure.

During the procedures, images and other data can be stored in the data storage device 116. The data storage device 116 may be embodied in hard disk drives, solid state memories, any other type of non-transitory computer readable storage medium. The data storage device 116 may also be distributed or partitioned across multiple local and/or remote storage devices. The data storage device 116 may include a data store. As used herein, a "data store" can refer to any data structure (and/or combinations of multiple data structures) for storing and/or organizing data, including, but not limited to, relational databases (e.g., Oracle databases, MySQL databases, etc.), non-relational databases (e.g., NoSQL databases, etc.), key-value databases, in-memory databases, tables in a database, and/or any other widely used or proprietary format for data storage.

Figure 2:
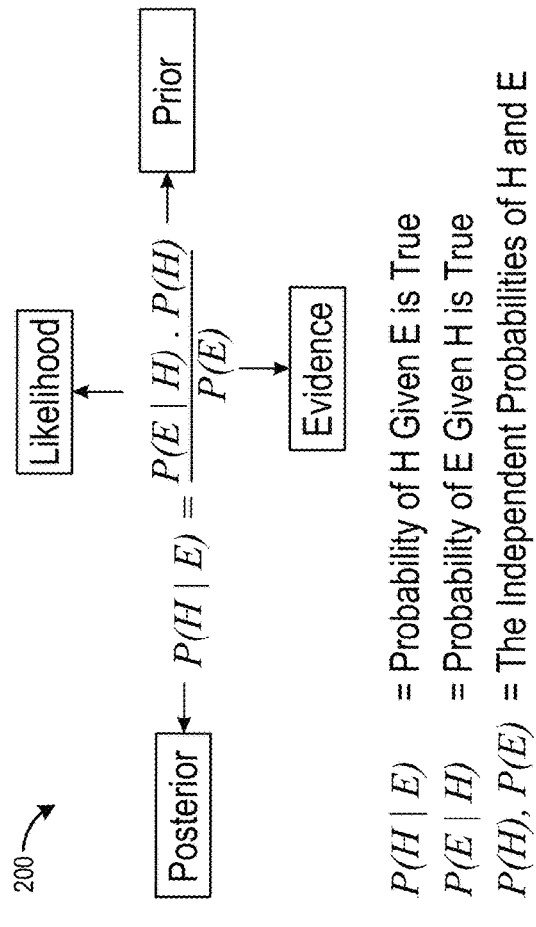
FIG. 2 depicts an equation that can be used in Bayesian inference and a Bayesian diagram.
Figure 2:
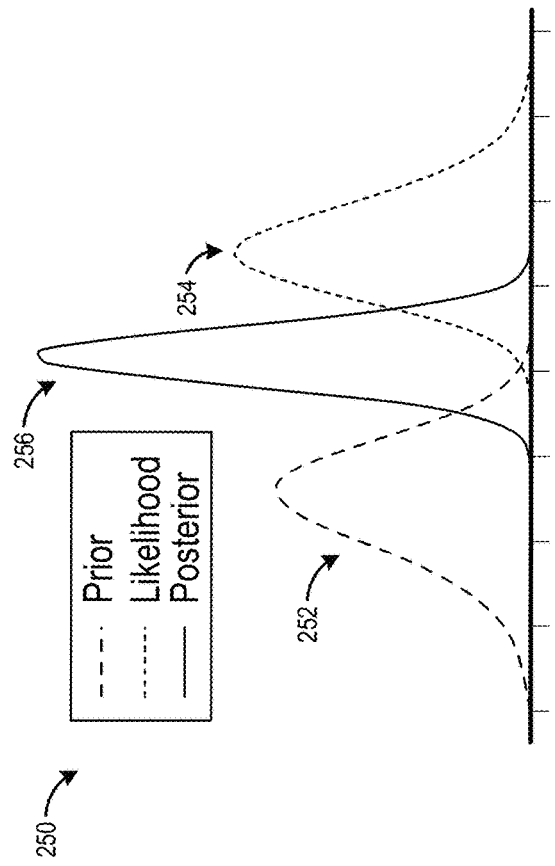

FIG. 2 depicts an equation 200 used in Bayesian inference and a Bayesian diagram 250. The equation 200 can be Bayes' theorem. Bayesian inference is a method of statistical inference in which the equation 200 can be used to update the probability for a hypothesis as more evidence or information becomes available. Bayesian inference can use prior knowledge, in the form of a Prior distribution, in order to estimate posterior probabilities.

Bayesian inference can derive the posterior probability as a consequence of two antecedents: (i) a prior probability and (ii) a likelihood function derived from a statistical model for the observed data. Bayesian inference can compute the posterior probability according to the equation 200. In the equation 200, H can refer to a hypothesis whose probability may be affected by evidence (E); P(H) can refer to the prior probability, which can estimate the probability of the hypothesis before the current evidence is observed; E can refer to the evidence, which can correspond to new data that was not used to determine the prior probability; P(H|E) can refer to the poster probability, which is the probability of H given E (after E is observed); P(E|H) can refer to the probability of observing E given H, which can be referred to as the likelihood; and P(E) can be referred to as the marginal likelihood.

The Bayesian diagram 250 can include a prior distribution 252, a likelihood distribution 254, and the posterior distribution 256. The prior distribution 252 can reflect the prior probability, which, as mentioned herein, can estimate the probability of the hypothesis before the current evidence is observed. The likelihood distribution 254 can reflect the probability of observing the evidence given the hypothesis. The posterior distribution 256 can reflect the probability of the hypothesis given the evidence. As shown, given the priors and the evidence, the mean and the standard deviation get tighter in the posterior distribution 256.

Figure 3:
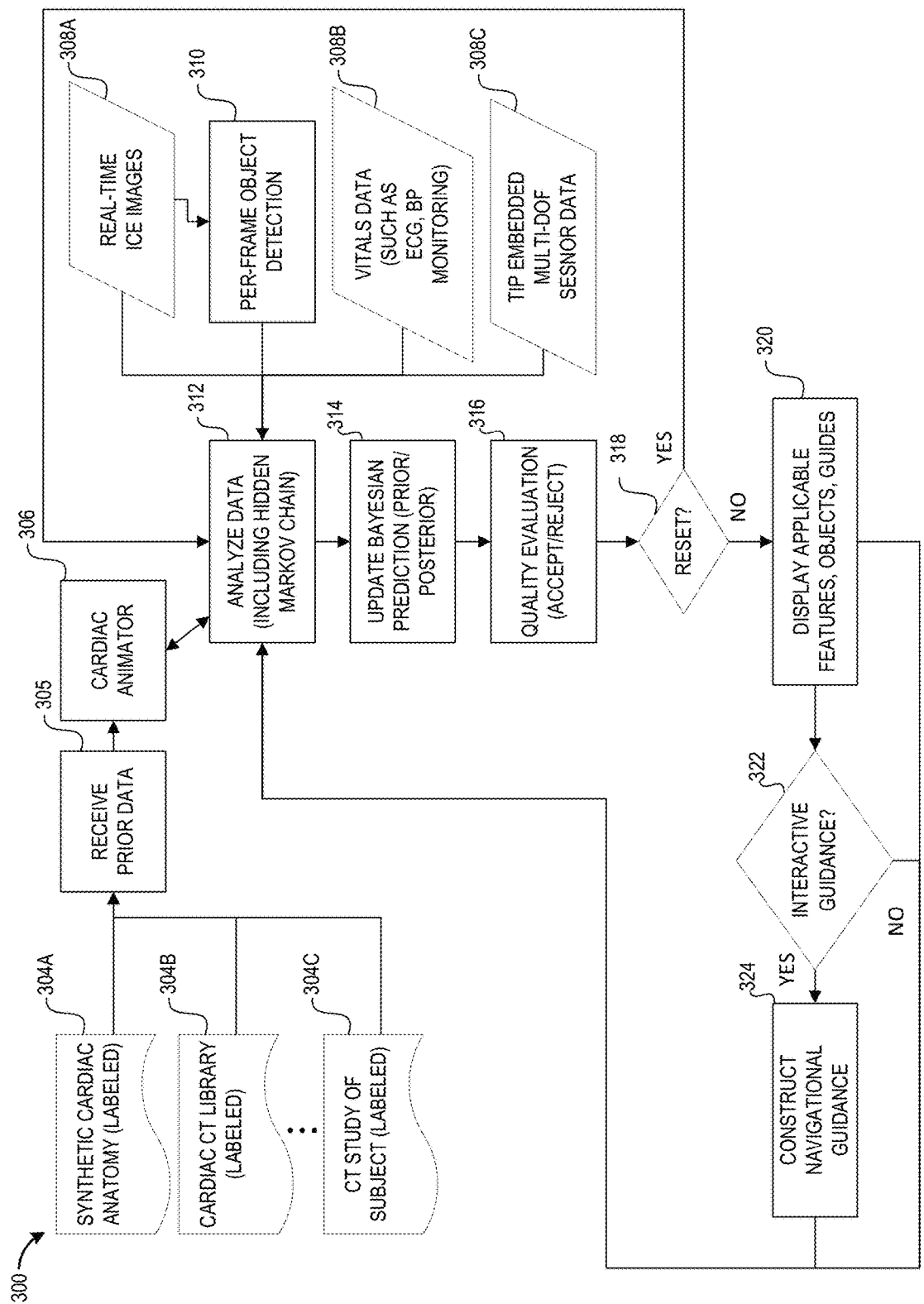
FIG. 3 is a flow chart depicting an example of a method for Bayesian anatomically-driven, artificial-intelligence based intracardiac echocardiography objection detection and prediction.

FIG. 3 is a flow chart depicting a method 300 for Bayesian anatomically-driven, artificial-intelligence based intracardiac echocardiography objection detection and prediction. With respect to the method 300, alternate implementations are included within the scope of the embodiments described herein in which elements or functions may be deleted, executed out of order from that shown, or discussed, including substantially concurrently or in reverse order, depending on the functionality involved.

At block 305, prior data can be received. The Bayesian prediction system 104 can receive prior data, such as, but not limited to, a synthetic volumetric model of the heart 304A, a volumetric image library of cardiac CT volumes 304B, and/or CT data of the subject 304C. The Bayesian prediction system 104 can make a hypothesis based on initial models, such as, but not limited to, a synthetic volumetric model of the heart 304A, a volumetric image library of cardiac CT volumes 304B, and/or CT data of the subject 304C, each of which can be pre-labeled, as a starting point. Each of the data sets 304A, 304B, 304C are progressively more specific to whichever subject will undergo an interventional cardiac procedure (such as an ablation, device implant, etc.). In some embodiments, the data sets 304A, 304B, 304C do not need to be extensive. The data sets 304A, 304B, 304C can be representative of cardiac volumetric representation and feature locations. The volumetric representations can be used such that any plane at any angle can be sliced from the representation and labels can be assigned into the slice.

Figure 4:
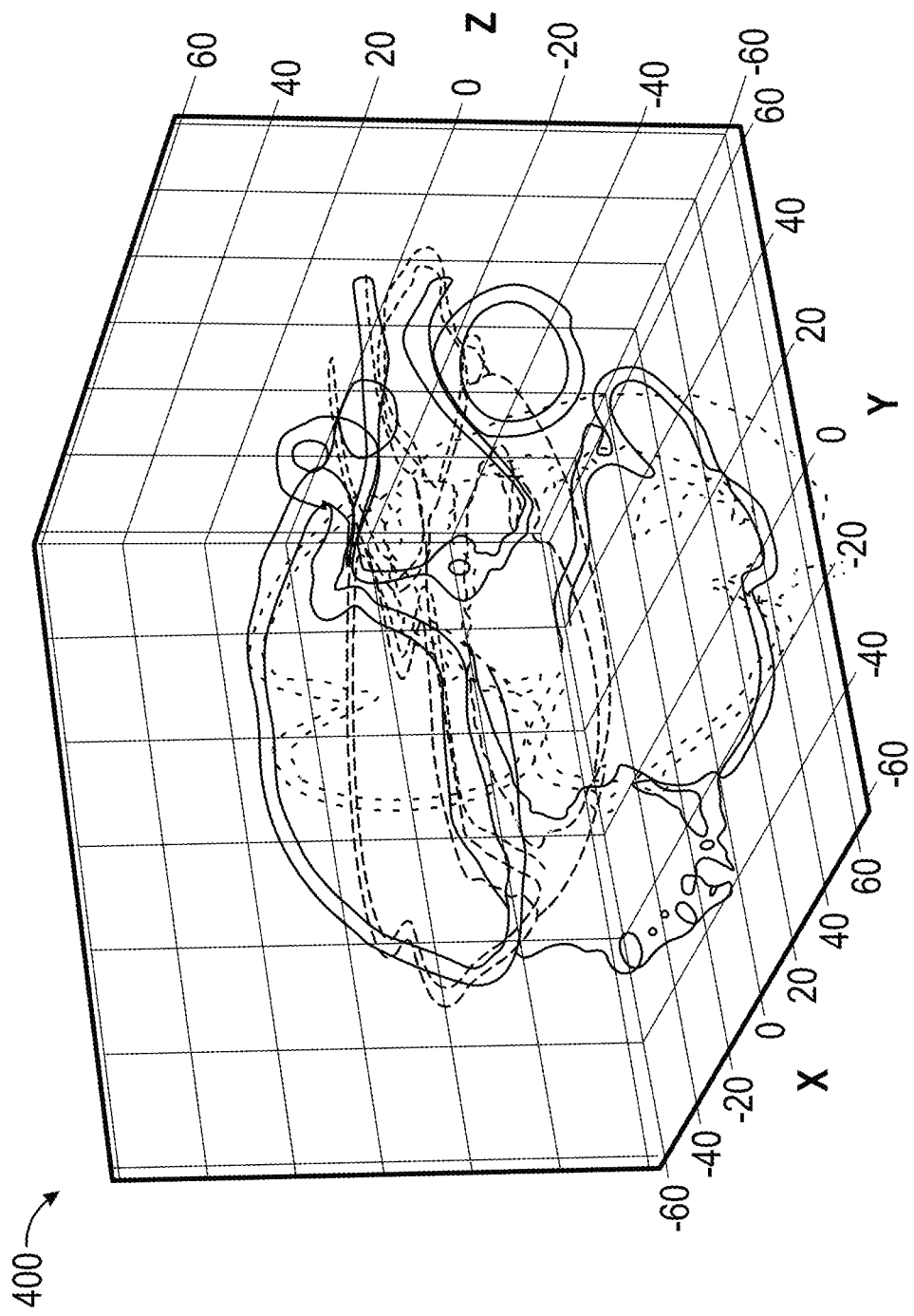
FIG. 4 depicts an example of a volumetric model of the heart.

Additional details regarding a volumetric model of the heart and slices are described herein, such as with respect to FIG. 4. The Bayesian prediction system 104 can determine an anatomical model from at least one or more of the data sets 304A, 304B, 304C. The Bayesian prediction system 104 can store the anatomical in the data storage device 116.

The Bayesian prediction system 104 can determine a prior distribution from at least one of the synthetic volumetric model of the heart 304A, the volumetric image library of cardiac CT volumes 304B, and/or the CT data of the subject 304C. The Bayesian prediction system 104 can determine a set of prior distributions. In some embodiments, each prior distribution can represent a distribution on a variable, such as the X location of a centroid for a first label, a Y location of a centroid for second label, etc. The Bayesian prediction system 104 can store the set of prior distributions in the data storage device 116.

At block 306, a cardiac animator can be applied. A mathematical function may be used for animating the static cardiac volume and/or specific images of the subject. Additionally or alternatively, volumetric video imaging of any sample subject can be received. It can be typical for involved cardiac procedures that prior CT imaging would have been performed; however, the method 300 does not require that as a precondition. When utilized, the mathematical function can be synchronized with instrumentation readout of what phase of the cardiac cycle a patient's heart is in. Alternatively, an analysis of identified objects during the live imaging itself can be analyzed to extract bounds on any periodic movement of the centroids of their bounding boxes and utilized to adjust the parameters of the mathematical function to animate the reference cardiac volume to synchronize with measured or computed periodicity parameters. The block 306 for animating the cardiac volume can be optional. The Bayesian prediction system 104 can use the data from the cardiac animator to make an initial hypothesis.

During live ICE imaging, the Bayesian prediction system 104 can start with a basic hypothesis of what might be visible in the first image. The initial hypothesis may start with a typical a home view during intracardiac echocardiography at an assumed imaging angle and depth. The probability of the initial hypothesis before the current evidence is observed can be referred to as a Prior. In some embodiments, the initial hypothesis can indicate a position in the right atrium and expected feature locations in either 2D or 3D depending on the type of imaging catheter being used.

The likelihood of each object's visibility can be modeled via a binomial distribution, since it's either visible or not, while its Prior probability distribution can then be modeled via its conjugate Prior, a Beta distribution.

The initial hypothesis can include initial relative location estimates for each predicted feature. The likelihood of the centroid of each bounding box of each predicted feature, since it may have spatial uncertainty, can have uncertainty in each of the dimensions being imaged, such as, (X, Y) coordinates for 2D images, (X, Y, Z) coordinates for 3D images, or any (X, Y)/(X, Z)/(Y, Z) coordinate for orthogonal views centered at the origin. However, for 3D imaging, any planar cut through a 3D volume can safely be modeled by keeping all 3 dimensions (X, Y, and Z) of the centroid in the model. An appropriate model for such a centroid for intracardiac imaging can be a multivariate (2 variables for 2D imaging, and 3 variables for 3D imaging) Gaussian distribution (also known as multivariate Gaussian (MVG)) distribution. With a multivariate Gaussian prior distribution as a starting point, Bayesian analysis can be applied with a multivariate Gaussian posterior distribution.

Elements of the initial prior distribution may be discarded in favor of an observed prior distribution that can be driven by statistical data, for example, the average of the first N (such as 2 to 10) frames of intracardiac images from substantially real-time ICE imaging. However, that distribution can still be fitted into an anatomical framework to make predictions on where each out-of-frame object/feature may be located and their binomial (un) certainty of presence (yes/no) and Gaussian spatial (un) certainty. As used herein, an "out-of-frame" object or feature can refer to an object or feature that is occluded in an image and/or outside of the image.

At block 310, during substantially real-time ICE imaging, each 2D frame or 3D volume (or its multi-planar views) can be analyzed by the AI object detector 122, which can make predictions on what features and/or objects are visible. These could be heart chambers (such as, right/left atrium, right/left ventricle), walls (such as, inter-atrial, inter-ventricular septum, atrial, or ventricular walls), valves (such as, tricuspid, mitral, aortic, or pulmonary valves), or artificial objects (such as, other catheters, devices in process of being implanted, wires, etc.). However, in some embodiments, unlike in typical AI-based object detection systems, these initial predictions may not be displayed on screen, and instead may only be analyzed to generate a first posterior distribution. The AI object detector 122 can make predictions regarding the respective locations of detected objects/features. The AI object detector 122 can predict a single confidence score of object identification and its bounding box location.

The AI object detector 122 can be trained in advance to identify features and objects of interest (such as those described herein) to a level of accuracy (such as satisfying a particular likelihood threshold) using labeled images from actual in vivo studies. The AI object detector 122 can include, but is not limited to, a two-step region-proposal and analysis system, a single-shot detection architecture, and/or a You Only Look Once (YOLO) object detection system. The AI object detector 122 can be (1) usable in run-time without significant latency (such as satisfying a particular latency threshold) and (2) predict in-frame objects/features and their locations with reasonable accuracy (such as satisfying a particular likelihood threshold).

At block 312, data can be analyzed. The Bayesian prediction system 104 can receive substantially real-time ICE images 308A and data from block 310 that performs per-frame object detection. The Bayesian prediction system 104 can receive an intracardiac echocardiography image 308A of the subject based at least in part on data from an intracardiac echocardiography catheter device. The Bayesian prediction system 104 can receive, from the AI object detector 122, (i) a predicted feature or object identified in the intracardiac echocardiography image and (ii) a location of the predicted feature or object relative to the intracardiac echocardiography image 308A.

At block 314, the Bayesian prediction can be updated. The Bayesian prediction system 104 can determine a set of posterior predictions from at least (i) a Bayesian method, (ii) the set of prior distributions, (iii) the intracardiac echocardiography image, (iv) the predicted feature or object, and (v) the location of the predicted feature or object. A posterior prediction from the set of posterior predictions can indicate a probability distribution associated with the predicted feature or object. In some embodiments, the Bayesian prediction system 104 can determine the set of posterior predictions from at least the anatomical model. A posterior prediction from the set of posterior predictions can indicate a probability distribution associated with a predicted feature or object not identified in the intracardiac image (such as an out-of-frame feature or object in the anatomical model) and a location of the predicted feature or object relative to the intracardiac echocardiography image.

Additional optional data that can be received at block 312 for analyzing data can include vitals data 308B and/or catheter-tip embedded multi-DOF sensor data 308C. In some embodiments, degrees of freedom sensor data 308C associated with the intracardiac echocardiography catheter device can include data related to vertical traverse, rotational traverse, radial traverse, pitching, yawing, and/or rolling. Vitals data 308B can include, but is not limited to, electrocardiogramd/or blood pressure (BP) monitoring data. At block 312 for analyzing data, the Bayesian prediction system 104 can use the vitals data 308B to track, substantially in real time, the cardiac cycle of the heart (such as, systole, diastole, isovolumic relaxation, inflow, isovolumic contraction, ejection, etc.). The Bayesian prediction system 104 can determine, from the vitals data, a cardiac cycle. At block 312, the Bayesian prediction system 104 can use the catheter-tip embedded multi-DOF sensor data 308C to determine a position, movement, and/or angle of imaging from the catheter tip. The Bayesian prediction system 104 can determine an orientation from the degrees of freedom sensor data. The optional data 308B, 308C can be used by the Bayesian prediction system 104 to either increase or decrease confidence during a Bayesian update from prior to posterior. With the additional data 308B, 308C, the Bayesian prediction system 104 can improve the quality of feature/object identification and/or their spatial location via modeling into the MVG probability distribution model of the latter.

At blocks 312 and 314, the Bayesian prediction system 104 can keep a running track of the following pieces of data. The tracked data can include per frame object identification and spatial location information from the AI object detector 122. The tracked data can include past N frames statistical data (such as running in-frame/out-of-frame scores of features/objects), where N>=1. The tracked data can include past N frames Bayesian hypothesis parameters: (1) for AI-identified object visibility: binomial likelihood result (such as a yes/no detection satisfying a confidence threshold) and Beta prior parameters (alpha and beta); (2) for AI-identified object spatial location: MVG parameters; (3) for fully occluded or predicted objects: a confidence score of their presence and location again via parameters noted in the preceding items 1 and 2; and/or (4) imager location and its imaging plane estimation, by correlating back to the anatomical model and utilizing it to create additional confidence to input into an internal Markov model. Additional details regarding updating prior/posterior beta probability distribution's parameters are described herein, such as with respect to FIG. 7. Additional details regarding updating spatial coordinates based at least in part on object location are described herein, such as with respect to FIG. 8.

At blocks 312 and 314, in some embodiments, the Bayesian prediction system 104 can advantageously use a Markov chain due to the periodic nature of cardiac rhythms. An observed periodicity over M frames of imaging data that include a full heart cycle can be used to create predictions for what will be in-frame in the next Y frames and fed into the Bayesian posterior analysis. In some embodiments, a Markov chain Monte Carlo (MCMC) can be used by the Bayesian prediction system 104 in some implementations for predictive modeling based on any Bayesian posterior computed by the Bayesian prediction system 104. The Bayesian prediction system 104 can determine the set of posterior predictions further comprises applying an MCMC method. The Bayesian prediction system 104 can apply an MCMC method, such as a Metropolis-Hastings algorithm, to obtain a sequence of random or pseudo-random samples to estimate a posterior probability distribution. The Bayesian prediction system 104 can add new samples to the sequence in two steps: first, a new sample can be proposed based on the previous sample; second, the proposed sample is either added to the sequence or rejected depending on the value of the probability distribution at that point. The Bayesian prediction system 104 can use the resulting sequence to approximate the posterior distribution.

The Bayesian prediction system 104 can determine a Markov chain comprising a first state corresponding to a first predicted feature or object and a second state. In some embodiments, the second state can correspond to an out-of-frame predicted feature or object, a cardiac cycle, or an orientation. The Bayesian prediction system 104 can determine the set of posterior predictions by feeding the Markov chain into the Bayesian method. Additional details regarding updating a Markov model (such as hidden Markov chain) are described herein, such as with respect to FIG. 9.

In some embodiments, the hidden Markov chain does not update a user-display directly. Instead the hidden Markov chain can be fed into the Bayesian posterior calculations. The Bayesian posterior calculations can be further analyzed by the Bayesian prediction system 104 prior to a decision to display or not display information.

At block 316, a quality evaluation can be performed. The Bayesian prediction system 104 can determine that a probability distribution satisfies a threshold. The Bayesian prediction system 104 can perform a quality evaluation and decide whether data quality from the posterior distribution satisfies a threshold to merit object detection and location information display (such as displaying on display device 110, such as an IDDS screen within an interventional cardiology suite). Quality metrics that would be evaluated here may already have been computed at the previous analysis blocks 312, 314 (such as a temporal $R/\wedge 2$ or other commonly used statistical measures, as described herein) or can be computed at the present block 316 (such as an uncertainty prediction measure such as confidence interval of Bayesian posterior prediction of objects and their spatial locations versus an AI-system detected object(s) and their observed locations according to the AI object detector 122). Objects and their spatial locations that satisfy pre-defined thresholds (such as an 'Accept/Reject' threshold setting) can then be allowed to be displayed. Similarly, an evaluation metric for quality of prediction of out-of-frame objects vs observed data as compared to predicted data can be used. Additional details regarding quality evaluation can be described herein, such as with respect to FIG. 10.

During the course of the catheter movement, the Bayesian prediction system 104 can constantly update, identify objects, update hypotheses and relative position in volumetric labeled space of an anatomical map to chart a course (while satisfying thresholds) to predict objects/features, as described herein. Based at least in part on a satisfied posterior prediction, the Bayesian prediction system 104 can update the anatomical mode. The Bayesian prediction system 104 can assign a location and an orientation to a device object (such as the ICE imaging tip 124) in the anatomical model. In some embodiments, the Bayesian prediction system 104 can use a pose estimation technique to determine the location and/or orientation of an object. The Bayesian prediction system 104 can reconstruct projection rays from the image points; for each projection ray and 3D contour: estimate the nearest point P1 of the ray R to a point on the contour, if (n==1) choose P1 as actual P for the point-line correspondence, else compare P1 with P: if the distance (P1, R) is smaller than distance (P, R) then choose P1 as new P; use (P, R) as correspondence set; estimate pose with this correspondence set; and transform the contours.

At block 318, a reset can be determined based at least in part on the quality evaluation. If the Bayesian prediction system 104 determines that a probability distribution fails to satisfy a threshold, then the Bayesian prediction system 104 can initiate a reset state, where initiating the reset state includes resetting a set of prior distributions. In some embodiments, the Bayesian prediction system 104 can reset itself to initial prior distribution(s). The Bayesian prediction system 104 can return to a last prior distribution that satisfied a threshold (such as a prediction that was displayed to a user). Additionally or alternatively, the Bayesian prediction system 104 can return to a last, valid prior distribution within a temporal and/or frame window; otherwise, the Bayesian prediction system 104 can return to initial prior distribution(s). If a significant degradation in identification or hypothesis quality occurs, the Bayesian prediction system 104 can automatically enter a Reset state and try to re-anchor itself within its anatomical map based at least in part on features and objects and their locations that satisfy one or more thresholds. If a Reset has been determined, the method 300 can return to block 312 to return to an earlier hypothesis. Otherwise, at block 320, features, objects, and/or navigational guidance can be displayed.

At block 320, applicable features, objects, and/or guides can be displayed. The Bayesian prediction system 104 can display, in a graphical user interface, (i) a label for the predicted feature or object associated with the location and (ii) the intracardiac echocardiography image. In the case of an out-of-frame feature or object, the Bayesian prediction system 104 can display, in the graphical user interface, a label for the predicted feature or object associated with a location, where the location is outside of the intracardiac echocardiography image. The Bayesian prediction system 104 can display, in the graphical user interface, a navigational element and an intracardiac echocardiography image, as described herein. Additional details regarding displaying applicable features, objects, and/or guides are described herein, such as with respect to FIGS. 11A-11C, 12A-12C, 13.

At block 322, if there is a request for interactive guidance, the method 300 can proceed to block 324 to construct navigational guidance. The Bayesian prediction system 104 can receive, via the graphical user interface, user input that indicates a target location within the anatomical model. In some embodiments, the graphical user interface can present an anatomical model of the heart and the user can request navigational assistance by selecting an object or feature in the presented anatomical model. Additionally or alternatively, the graphical user interface can present object/feature options (such as "right atrium (RA)," "tricuspid valve (TV)," etc.) and the graphical user interface can receive a selected option. Otherwise, the method 300 can return to block 312 to continue processing more frames, analyze incoming data, and update the hypothesis.

At block 324, the Bayesian prediction system 104 can construct navigational guidance. The navigational guidance can provide an indicator that can inform a clinician how to position the catheter to arrive at a target location. The Bayesian prediction system 104 can refer back to an anatomical model to determine the navigational guidance. The Bayesian prediction system 104 can determine a navigational element from a location/orientation of an object (such as the ICE imaging tip 1204) and a target location. The navigational element can indicate to a user a direction and/or movement to navigate the object. In some embodiments, the Bayesian prediction system 104 can represent the anatomical model and locations within the anatomical model as a graph model (such as a graph mesh and/or polygon mesh). The Bayesian prediction system 104 can use one or more algorithms to navigate the graph model and determine navigational elements. The Bayesian prediction system 104 can use graph navigational algorithms, a string pulling algorithm, and/or a steering algorithm. The Bayesian prediction system 104 can maintain an orientation of the object and navigate the object through polygons (such as rotation about X-axis, Y-axis, and/or Z-axis). The Bayesian prediction system 104 can determine a cell or node and a destination cell. In a navigation mesh, shared edges between two cells are also portal edges, which can be used by string pulling/steering algorithms. The Bayesian prediction system 104 can check which cell is closest to each point (starting and ending) using a tree data structure, such as an octree. The Bayesian prediction system 104 can apply a graph navigation algorithm, such as the A* algorithm. The Bayesian prediction system 104 can assign a cost and a heuristic to a cell; the closer the cell is to the destination, the less expensive it is; the heuristic can be calculated similarly but the heuristics of the previous cell can also be taken into account. The Bayesian prediction system 104 can keep a queue in descending order of cells based on their heuristics. The Bayesian prediction system 104 can apply string pulling/steering algorithms to determine a path from the queue of cells. The method 300 can return to block 312 to process in a loop and analyze incoming data and update the hypothesis and eventually display any constructed navigational guidance.

The systems and methods described herein may improve computer vision (a field of AI) technology related to AI-based object detection. In typical AI-based object detection systems, all predictions by AI-based object detection systems are automatically displayed. In contrast, the systems and methods described herein can use the initial predictions from an AI object detector may not be displayed on screen, and instead may be analyzed with Bayesian techniques. During a Bayesian predictive cycle where one goes from a prior to a posterior (which can then become a prior for the next cycle, unless there is a reset, in which case the system can start with a de novo prior), the prior can be informative because in addition to images and the per-frame object(s) detection the system can use (a) a "world view" from the anatomical models, (b) additional data, such as, vitals data (ECG, pulse, etc.) to indicate a cardiac cycle, and/or (c) a rolling longer-window over X number of frames to attempt to auto-detect cardiac cycle and motions associated with each cycle (if the system can figure it out, depending on how static the imaging tip is or how noisy/turbulent the environment is or image quality itself). This sort of an informative prior construction for intracardiac imaging AI can lead to more credible posteriors (which can lead to higher confidence displayed labels or guidance for in-frame/out-of-frame objects/features, the latter in particular being very reliant on the world-view and relative logical expectation of what's relatively where in typical cardiac anatomy. The Bayesian prediction system 104 can thus programmatically evaluate predictions from an AI object detector based at least in part on priors to determine which predictions to display and which predictions to prevent from being displayed. Accordingly, the systems and methods described herein may improve computer vision technology.

The systems and methods described herein may improve computer vision technology in intracardiac imaging and the functioning of a computer. As described herein, existing object and feature detection methods struggle in dynamically changing environments, such as intracardiac imaging. Detecting objects and features during intracardiac imaging is technically challenging due to a very large number of dynamically changing factors. Those factors can include imaging angle, imaging depth, focal depth and number of focal points, imaging aperture, image quality settings, and/or the cardiac environment itself (such as chamber deformations during systolic and diastolic phases, turbulent fluid flow, large variation in size, abnormalities, and/or wall or valve dynamics specific to particular subjects). Also as described herein, existing EAM systems lack the ability to (1) perform object detection and label objects/features within a heart, (2) predict future objects/features that could be seen as the clinician moves the catheter within the heart, and/or (3) provide directions to a clinician on how to get to other locations within the heart. The systems and methods using the Bayesian and other techniques described herein can enable object and feature detection in the challenging intracardiac environment and can enable a computer to perform better object detection in said environment. In particular, the Bayesian prediction system 104 can (1) perform object/feature detection and label objects within a heart, (2) predict future objects/features that could be seen as the clinician moves the catheter within the heart, and/or (3) provide directions to a clinician on how to get to other locations within the heart. Accordingly, the systems and methods described herein may improve intracardiac imaging technology and the functioning of a computer.

FIG. 4 depicts a volumetric model of the heart 400 is shown. The volumetric model of the heart 400 includes several (here three) orthogonal slices. The volumetric model of the heart 400 can be illustrative of an anatomical model used by the Bayesian prediction system 104 to make predictions, as described herein.

Figure 5A:
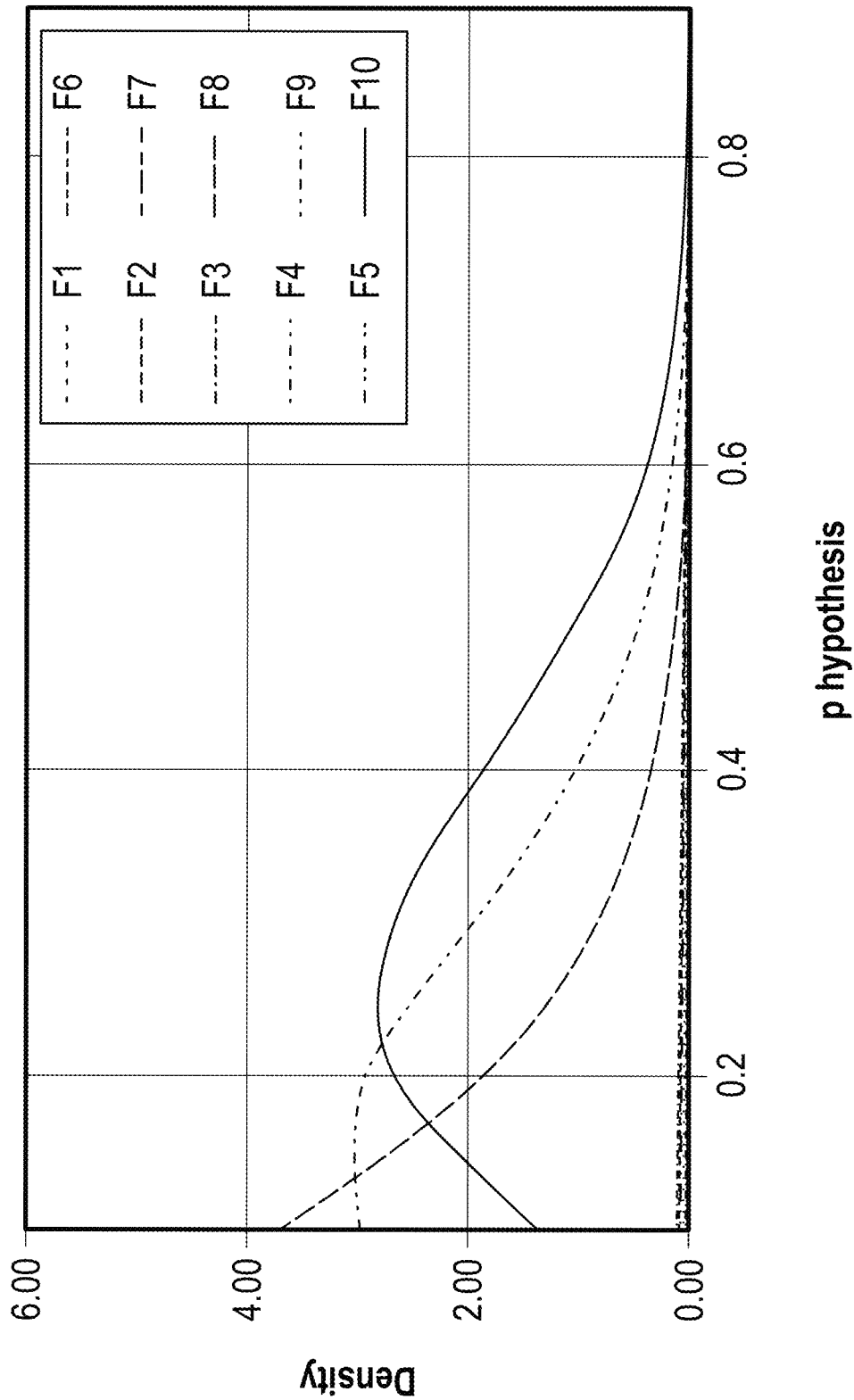
FIGS. 5A-5E depict charts showing Bayesian probability density during object or feature detection.
Figure 5B:
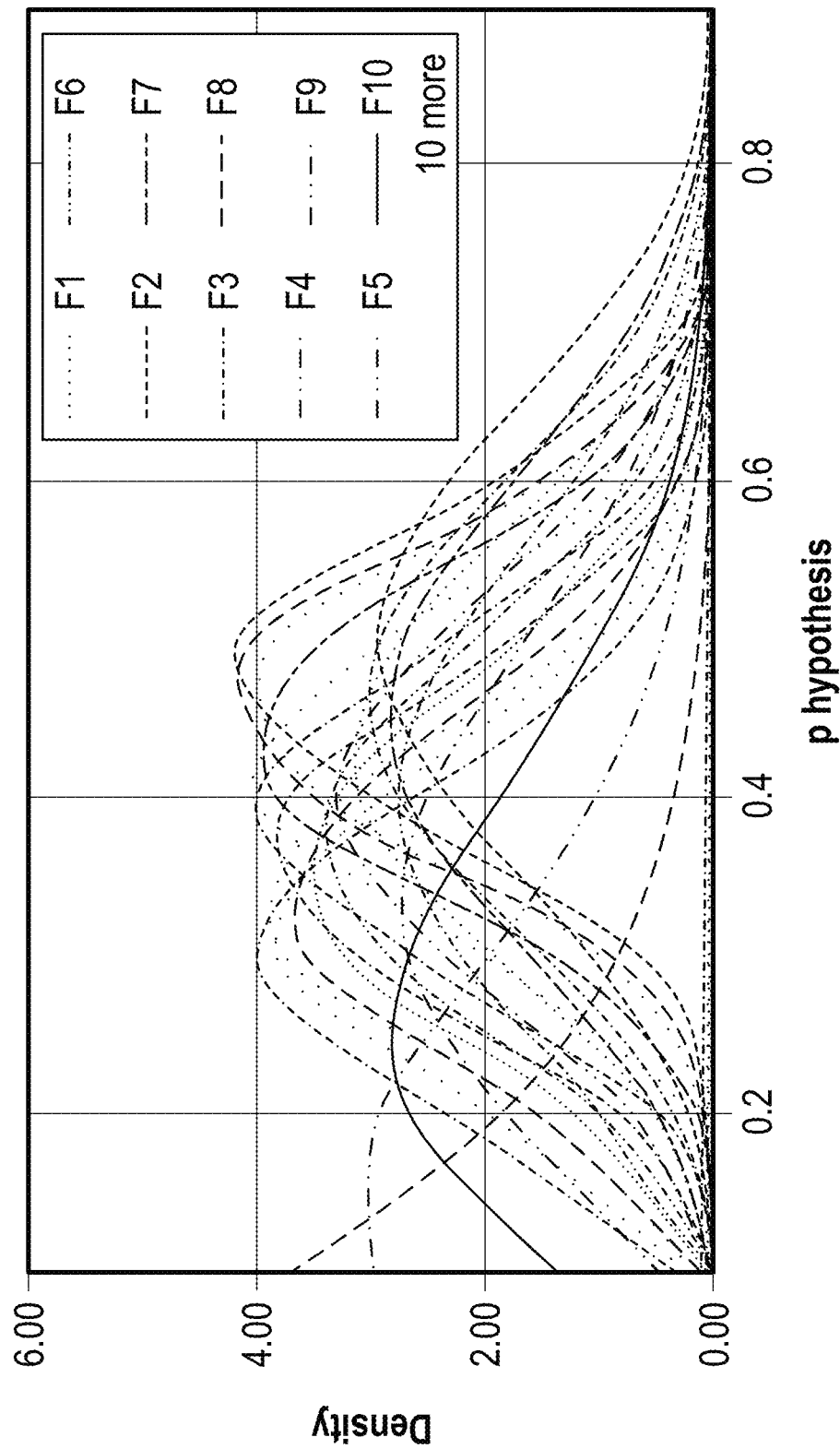
Figure 5C:
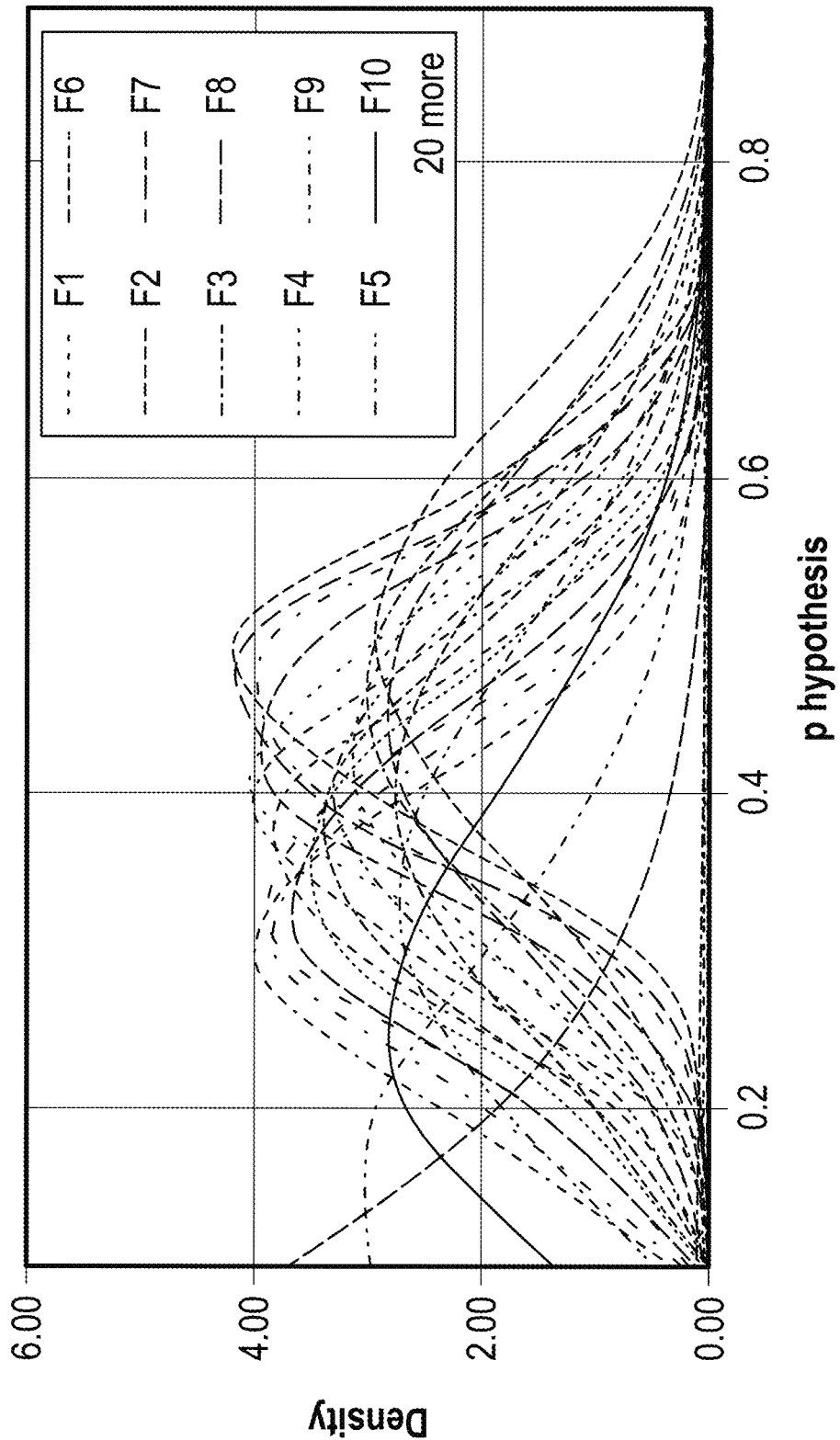
Figure 5D:
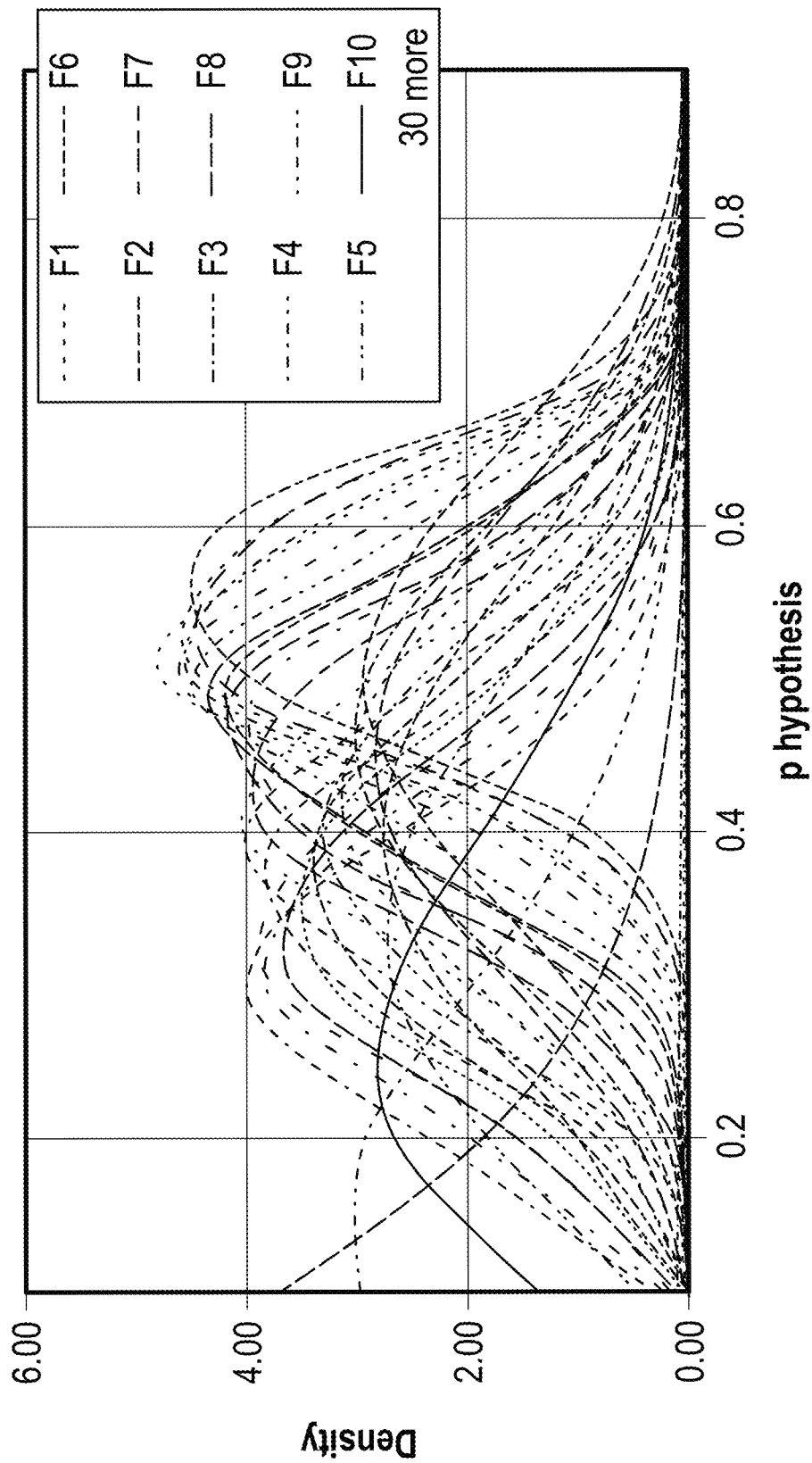
Figure 5E:
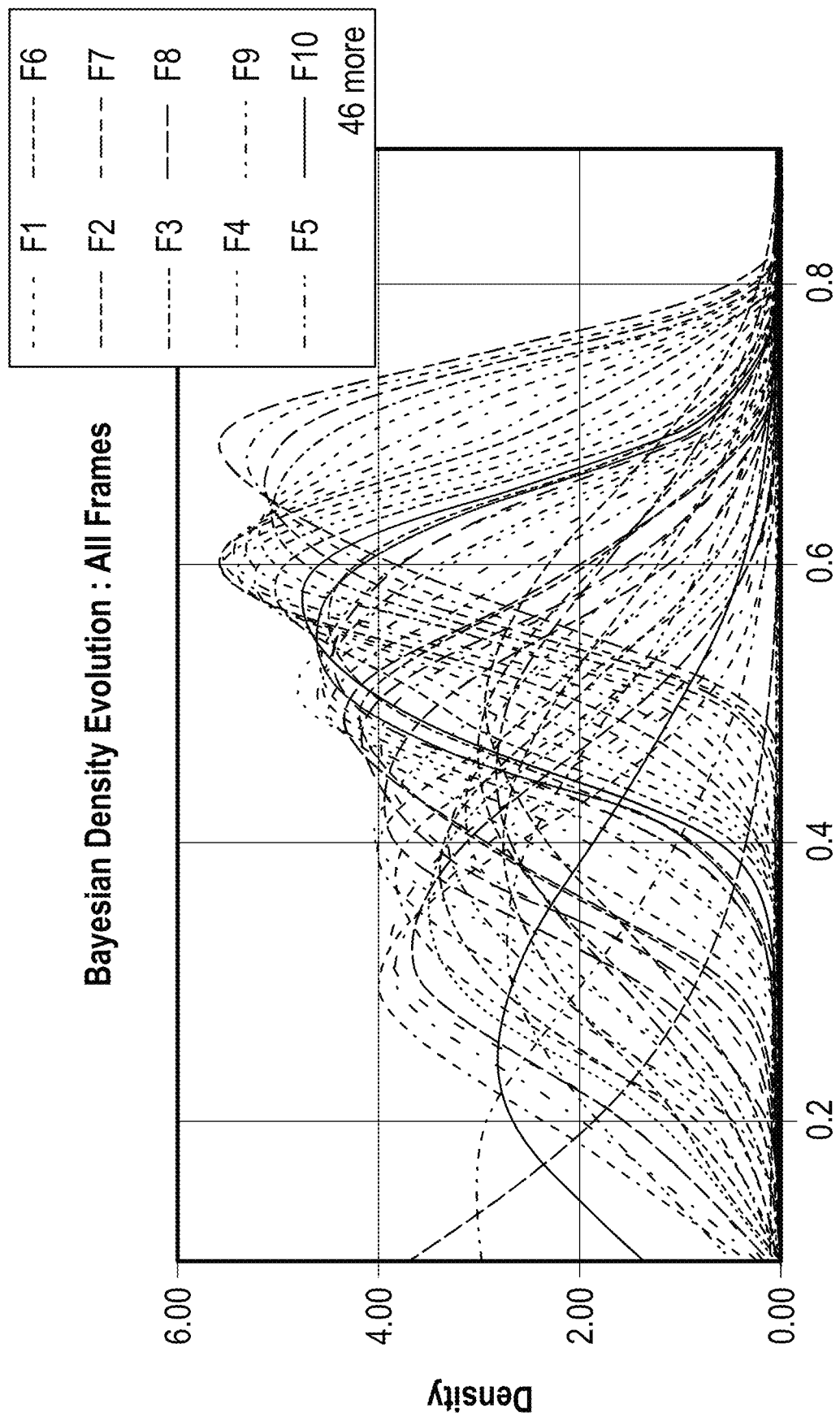

FIGS. 5A, 5B, 5C, 5D, and 5E depict charts showing Bayesian probability density during object or feature detection. In FIG. 5A, the probability density is shown in the Y axis and the probability of the parameter p can be shown in the X axis for the first N frames observed (here N=10). The prior probability distribution can be modeled via its conjugate prior, a Beta distribution. FIGS. 5B, 5C, 5D, and 5E can show the probability distribution for additional frames as N gets larger, and, specifically, N=20, N=30, N=40, and N=all frames, respectively.

Figure 6A:
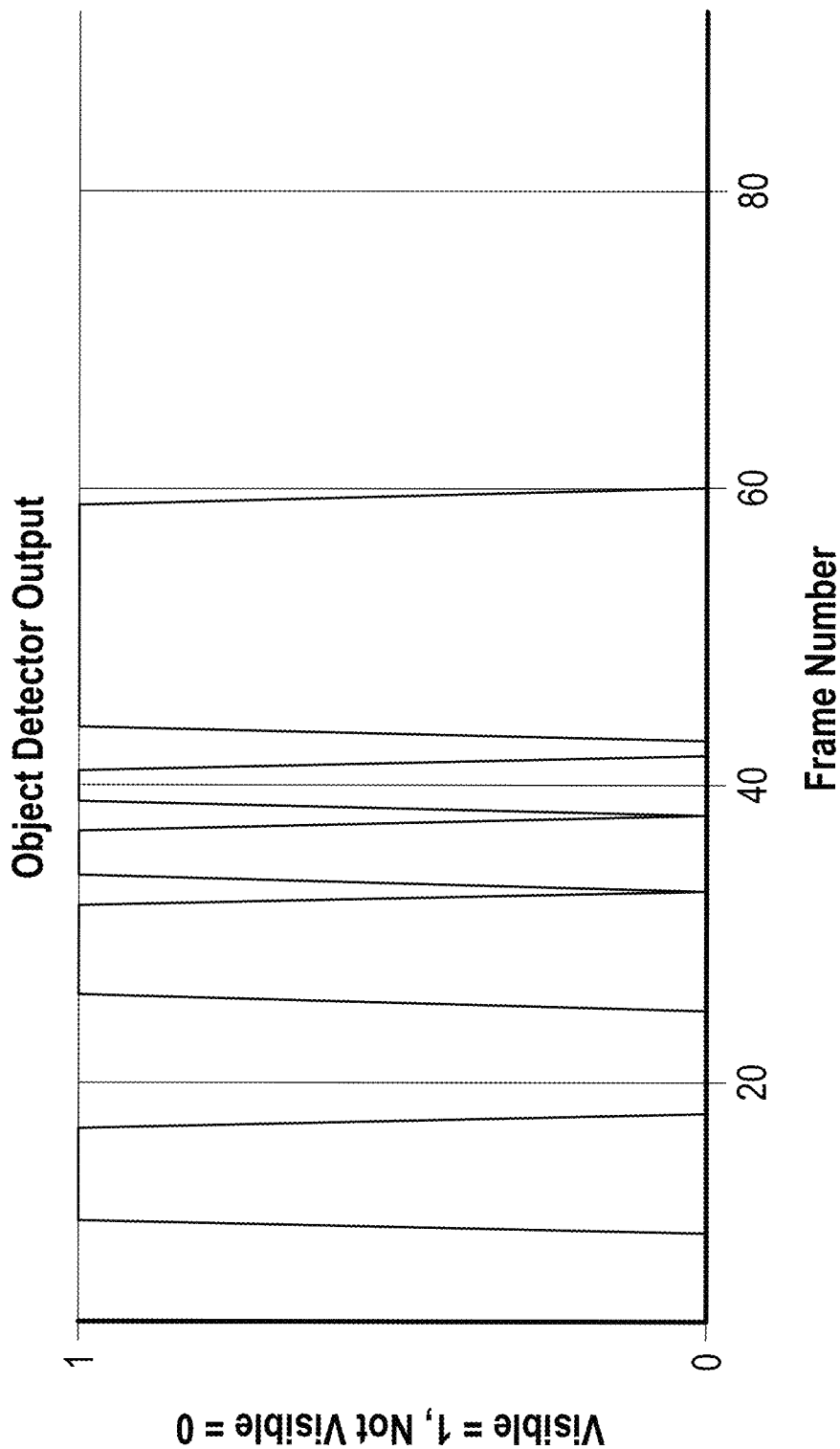
FIG. 6A depicts a chart showing object detector output for multiple frames.

FIG. 6A depicts a chart showing object detector output for multiple frames. In FIG. 6A, the chart shows object detector output for each frame. In the chart, visible is shown as a "1" and not visible is shown as a "0."

Figure 6B:
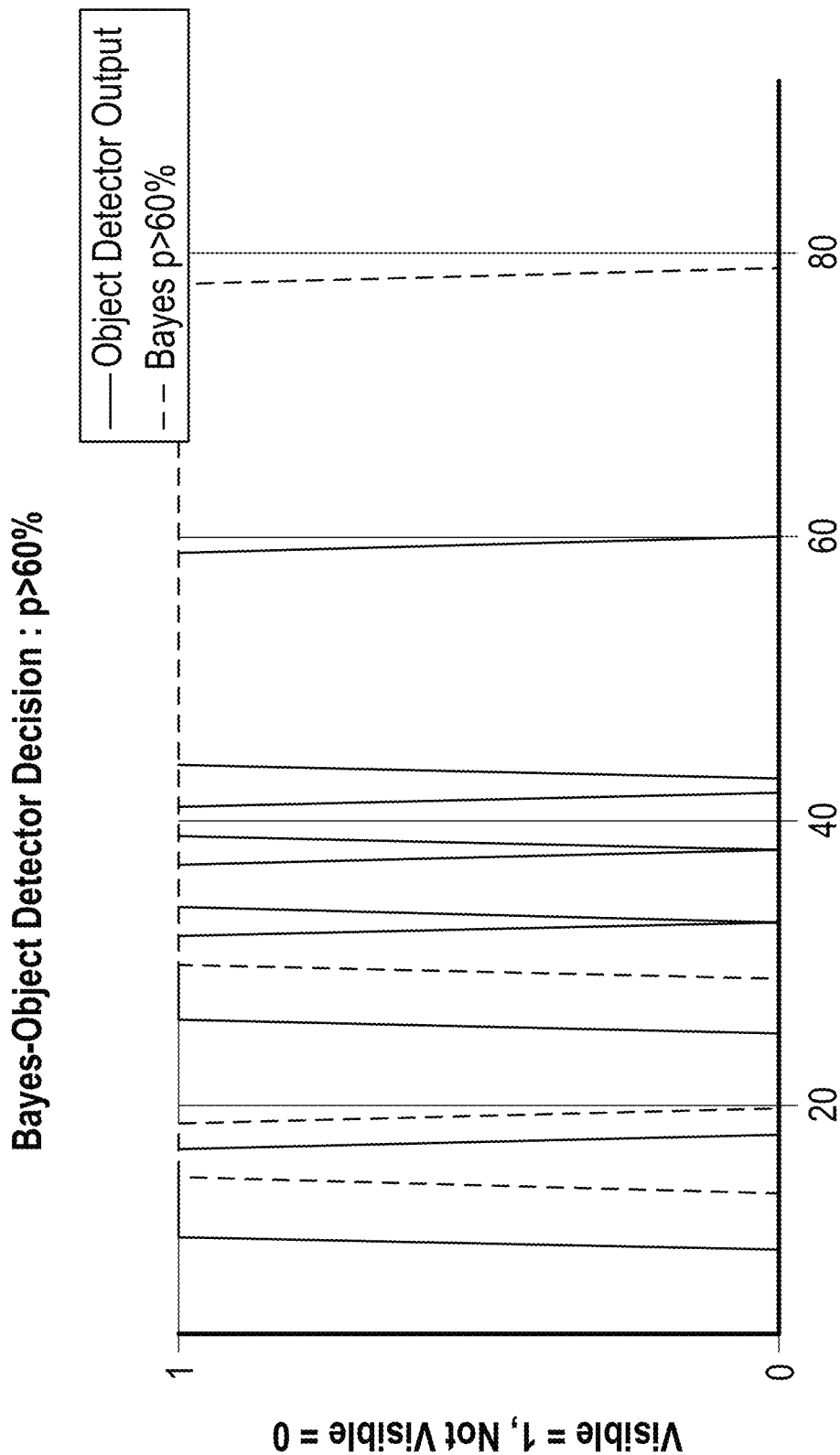
FIG. 6B depicts a chart showing Bayesian and object detector output for multiple frames.

FIG. 6B depicts a chart showing Bayesian and object detector output for multiple frames. In FIG. 6A, the chart shows object detector output for each frame and the Bayesian prediction for the output is p>60%. As shown, the AI object detector may detect an object/feature, but in some cases the Bayesian prediction may not satisfy a threshold, which can cause the Bayesian prediction system 104 to not display a corresponding object or feature label.

Figure 7:
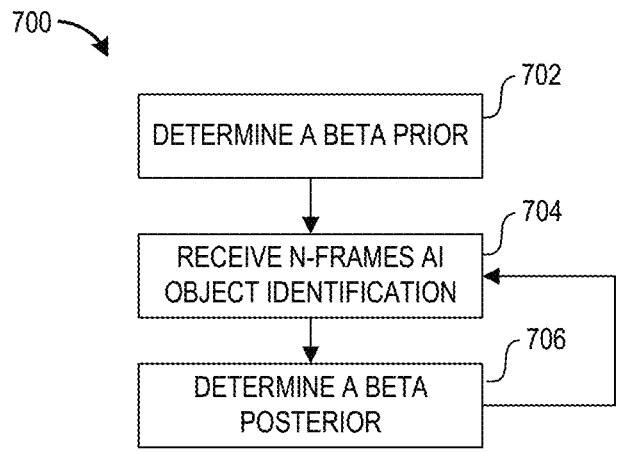
FIG. 7 is a flow chart depicting a method for updating prior/posterior Beta probability distribution's parameters.

FIG. 7 is a flow chart depicting a method 700 for updating prior/posterior Beta probability distribution's parameters. In FIG. 7, the flow chart shows how prior/posterior Beta probability distribution's parameters can be updated based on object detection by the Bayesian prediction system 104. The flowchart may not list all the affected parameters that can be updated.

At block 702, a Beta prior can be determined. The Bayesian prediction system 104 can determine Beta priors from previous object identification results. A Beta distribution can refer to a family of continuous probability distributions defined on the interval (0, 1) in terms of two positive parameters, denoted by alpha and beta. The Beta distribution can be the conjugate prior probability distribution for binomial distributions, which means that if the likelihood function is binomial and the prior distribution is beta then the posterior is also beta. As described herein, the Bayesian prediction system 104 can determine prior binomial likelihood result(s) (such as a yes/no identification) and corresponding Beta prior parameters (alpha and beta) for the result(s).

At block 704, N frames of AI object identification results can be received. The Bayesian prediction system 104 can receive per frame object identification information from the AI object detector 122 for one or more frames. In some embodiments, the Bayesian prediction system 104 can receive the past N frames of detected/not-detected features/objects from the AI object detector 122.

At block 706, a Beta posterior can be determined. The Bayesian prediction system 104 can determine Beta posteriors from the priors and the current evidence (the past N frames of detected/not-detected features/objects). In some embodiments, the Bayesian prediction system 104 can determine the Beta posterior from combining (such as multiplying) the prior density and the current likelihood. The Beta posterior can be proportional to the prior multiplied by the likelihood. As shown, the method 700 can loop back to block 704 to receive additional n-frames of data, which can be used to determine an updated Beta posterior where the previous posterior becomes the prior in a subsequent loop.

Figure 8:
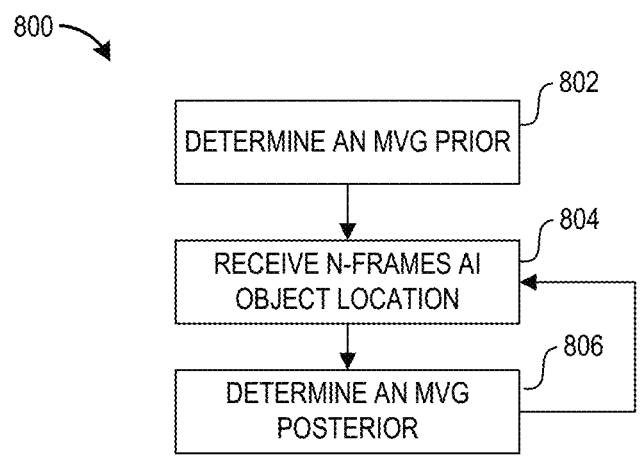
FIG. 8 is a flow chart depicting a method for updating multivariate Gaussian prior/posterior distributions for spatial location(s).

FIG. 8 is a flow chart depicting a method 800 for updating multivariate Gaussian prior/posterior distributions for spatial location(s). In FIG. 8, the flow chart shows how spatial coordinate(s) can be updated based on object location determined by the Bayesian prediction system 104. The flowchart may not list all the affected parameters that can be updated.

At block 802, a multivariate Gaussian prior distribution can be determined. The Bayesian prediction system 104 can determine a multivariate Gaussian prior distribution from previous object location results. The Bayesian prediction system 104 can use a multivariate Gaussian distribution to model centroids for intracardiac imaging. The Bayesian prediction system 104 can determine an initial hypothesis from initial relative location estimates for each prior feature.

At block 804, N frames of AI object location results can be received. The Bayesian prediction system 104 can receive per frame object location information from the AI object detector 122 for one or more frames. As described herein, the likelihood of the centroid of each bounding box of each predicted feature, since it may have spatial uncertainty, can have uncertainty in each of the dimensions being imaged, such as, (X, Y) coordinate for 2D images, (X, Y, Z) coordinate for 3D images, or any (X, Y)/(X, Z)/(Y, Z) coordinate for orthogonal views centered at the origin. However, for 3D imaging, any planar cut through a 3D volume can be modeled by keeping all three dimensions (X, Y, and Z) of the centroid in the multivariate Gaussian model.

At block 806, a multivariate Gaussian posterior distribution can be determined. The Bayesian prediction system 104 can determine multivariate Gaussian posteriors from the priors and the current evidence (the past N frames of object/feature locations). In some embodiments, the Bayesian prediction system 104 can determine the multivariate Gaussian posterior from combining the multivariate Gaussian posterior and the current likelihood. As shown, the method 800 can loop back to block 804 to receive additional n-frames of data, which can be used to determine an updated multivariate Gaussian posterior where the previous posterior becomes the prior in a subsequent loop.

Figure 9:
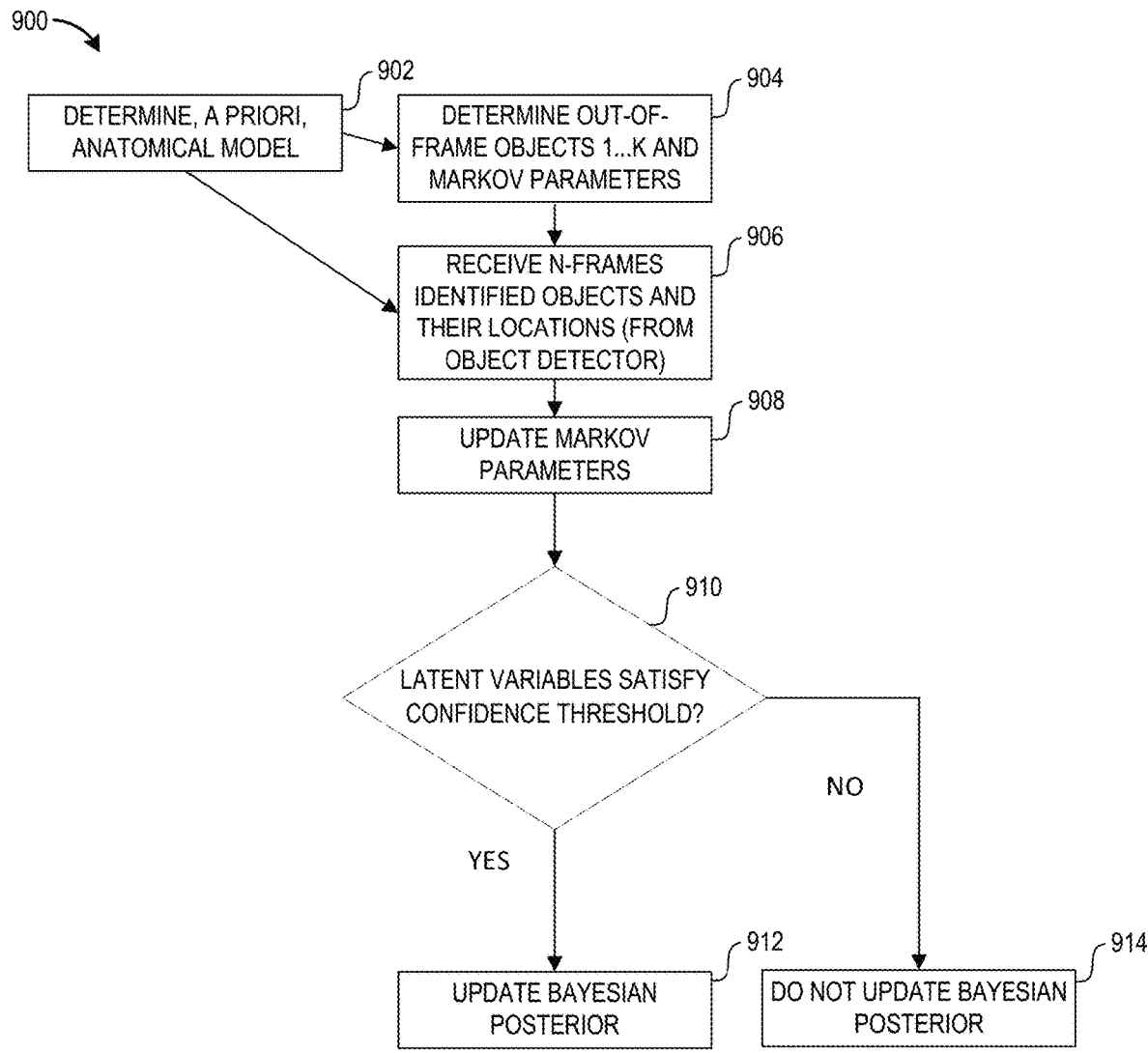
FIG. 9 is a flow chart depicting a method for updating a hidden Markov model of in-frame/out-of-frame objects or features.

FIG. 9 is a flow chart depicting a method 900 for updating a hidden Markov model (such as a hidden Markov chain) of in-frame/out-of-frame objects or features. At block 902, an anatomical model can be determined a priori. The Bayesian prediction system 104 can determine an anatomical model from data, such as, but not limited to, a synthetic volumetric model of the heart 304A, a volumetric image library of cardiac CT volumes 304B, and/or CT data of the subject 304C. In some embodiments, the Bayesian prediction system 104 can use imaging techniques to create an anatomical model, such as, but not limited to, image segmentation, image denoising, generation of mesh geometry, and/or smoothing operations.

At block 904, out-of-frame object(s)/feature(s) and Markov parameters can be determined. The Bayesian prediction system 104 can determine out-of-frame object(s)/feature(s) from the anatomical model and a starting position. For example, an initial hypothesis can indicate a starting position in the right atrium. Accordingly, the Bayesian prediction system 104 can determine out-of-frame object(s)/feature(s) from starting position in the right atrium by referencing the anatomical model. The Bayesian prediction system 104 can determine Markov parameters for an initial hypothesis and the out-of-frame object(s)/feature(s). To represent the out-of-frame object(s)/feature(s), the Bayesian prediction system 104 can determine a sequence of variables (also referred to as states), such that the probability of moving to the next state depends only on the present state and not on the previous states.

At block 906, N frames of AI object identification results and their respective locations can be received. The Bayesian prediction system 104 can receive per frame object identification information and location information of in-frame objects from the AI object detector 122 for one or more frames. The Bayesian prediction system 104 can determine a Markov chain comprising a first state corresponding to a first predicted feature or object and a second state corresponding to an out-of-frame predicted feature or object. Additional details regarding receiving frame information from an object detector are described herein, such as with respect to FIGS. 3, 7, and 8.

At block 908, updated Markov parameters can be determined. The Bayesian prediction system 104 can determine updated Markov parameters from the current Markov parameters and the current evidence. In some embodiments, the Bayesian prediction system 104 can multiply the current state vector by a transition matrix.

At block 910, it can be determined whether latent variables satisfy a confidence threshold. The Bayesian prediction system 104 can determine whether the state variables in a hidden Markov model satisfy a confidence threshold. If the latent variables satisfy a threshold, the method 900 can proceed to block 912 to update a Bayesian posterior. Otherwise, the method 900 can proceed to block 914 to not update a Bayesian posterior.

At block 912, a Bayesian posterior can be updated. The Bayesian prediction system 104 can feed the hidden Markov model (such as a Markov chain) into a Bayesian method that takes in a prior and the current evidence and outputs a posterior. As described herein, posteriors can be further analyzed by the Bayesian prediction system 104 to determine whether to display or not to display information.

Figure 10:
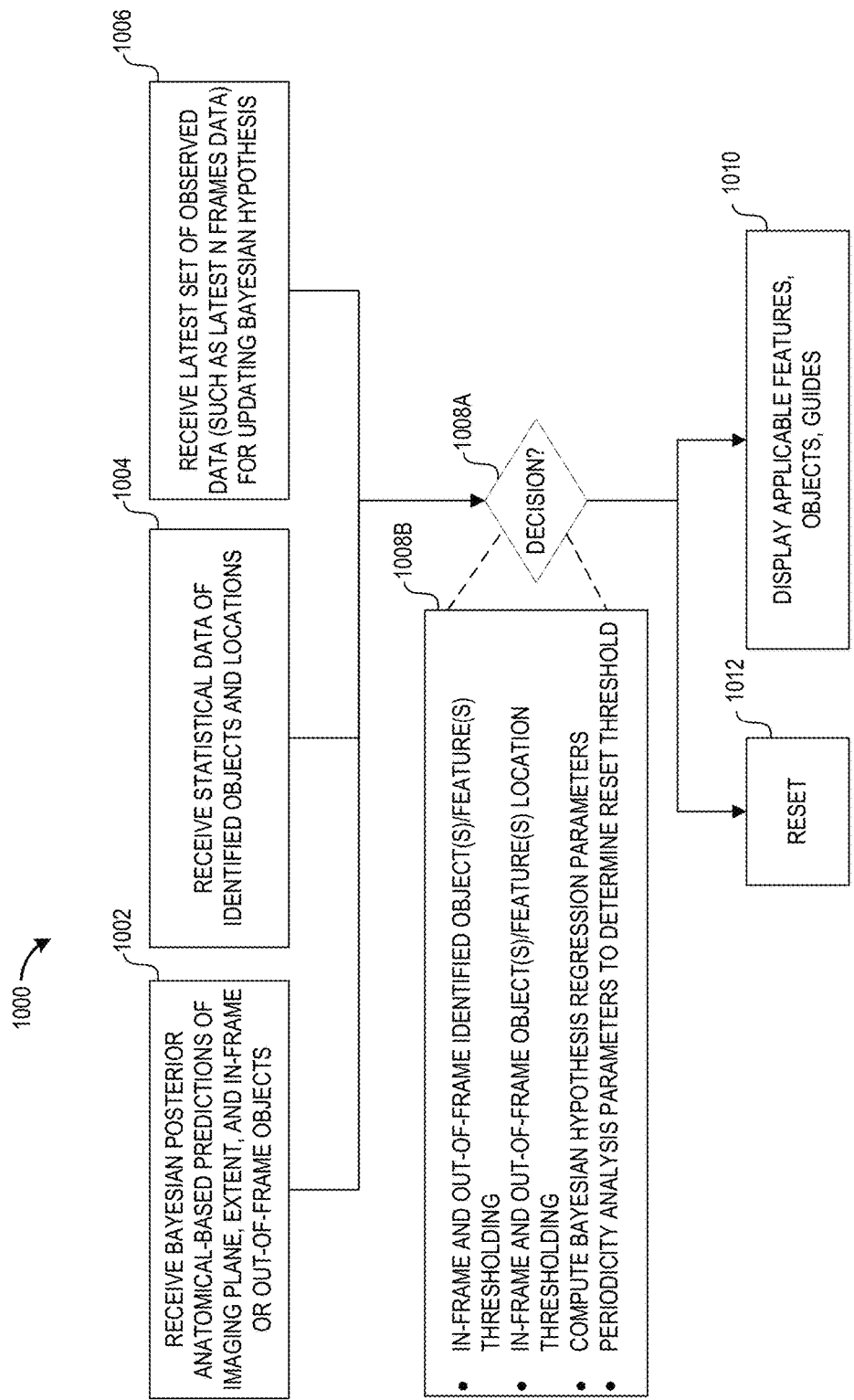
FIG. 10 is a flow chart depicting an example of a method for making quality evaluation decisions.

A flow chart of how to update a hidden Markov model of out-of-frame features and objects in 2D or 3D is shown in FIG. 10. The hidden Markov chain does not update a user-display directly. Instead the hidden Markov chain can be fed into the Bayesian posterior calculations. The Bayesian posterior calculations can be further analyzed by the system prior to a decision to display or not display information.

FIG. 10 is a flow chart depicting a method 1000 for making quality evaluation decisions. At block 1002, Bayesian posterior anatomical-based predictions can be received. As described herein, the Bayesian prediction system 104 can receive predictions regarding an imaging plane, extent (such as area covered by an object/feature), and/or in-fame or out-of-frame objects/features. As described herein, a posterior prediction from the set of posterior predictions can indicate a probability distribution associated with a variable, such as, but not limited to, a predicted feature or object, the X location of a centroid for a first label, a Y location of a centroid for second label, etc.

At block 1004, statistical data regarding identified objects and locations can be received. As described herein, the Bayesian prediction system 104 can maintain running in-frame/out-of-frame scores of features/objects, such as, but not limited to, cumulative scores or averages.

At block 1006, the latest set of observed data (such as latest N frames data) for updating a Bayesian hypothesis can be received. The Bayesian prediction system 104 can receive N frames of ICE images 308A. The Bayesian prediction system 104 can receive vitals data 308B (such as ECG data and/or BP monitoring data) and/or catheter-tip embedded multi-DOF sensor data 308C synchronized with frames.

At block 1008A, 1008B, a decision can be made. The Bayesian prediction system 104 can make a decision based at least in part on the Bayesian posterior anatomical-based predictions, statistical data regarding identified objects and locations, and/or the latest set of observed data. The Bayesian prediction system 104 can determine whether predictions regarding identified objects/features (both in view and out-of-view) satisfy one or more thresholds. The Bayesian prediction system 104 can determine whether the predictions regarding locations for objects/features (both in view and out-of-view) satisfy one or more thresholds. The Bayesian prediction system 104 can compare Bayesian posterior distributions to confidence interval thresholds. The Bayesian prediction system 104 can compute regression parameters for a Bayesian hypothesis. In some embodiments, the Bayesian prediction system 104 can form a prior distribution for multiple parameters, determine a likelihood of the data, and use Bayes theorem to determine the posterior distribution for multiple parameters. If the posterior distribution fails to satisfy a threshold, the method 1000 can proceed to block 1012 for a reset, otherwise, the method 1000 can proceed to block 1010 to cause a display of applicable features, objects, and/or guides, as described herein. The Bayesian prediction system 104 can apply periodicity analysis parameters to determine a reset threshold. At block 1012, a reset can be activated. At block 1010, applicable features, objects, and/or guides, can be displayed, as described herein.

Figure 11A:
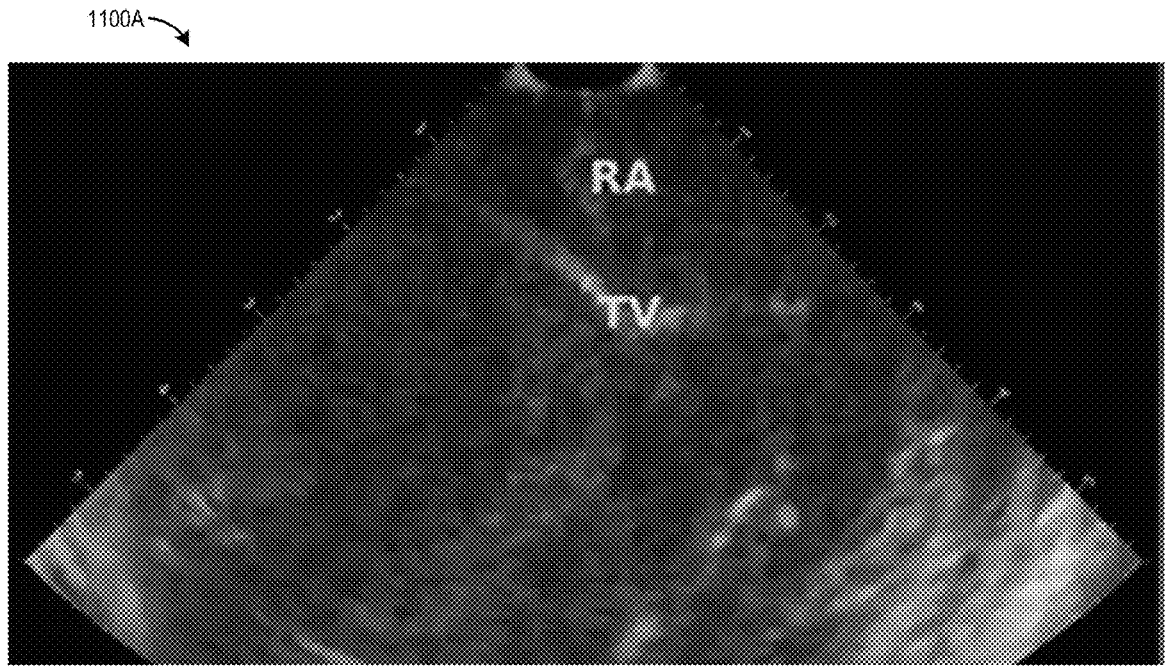
FIGS. 11A-11C depict examples of object/feature identification graphical user interfaces.
Figure 11B:
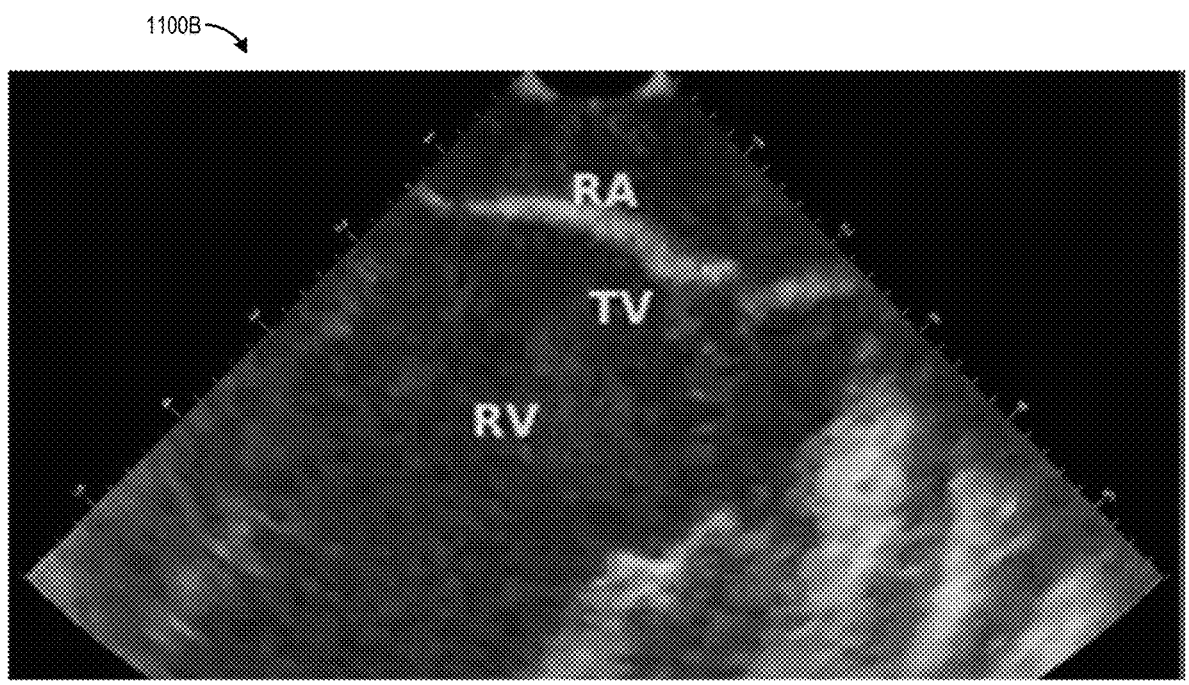
Figure 11C:
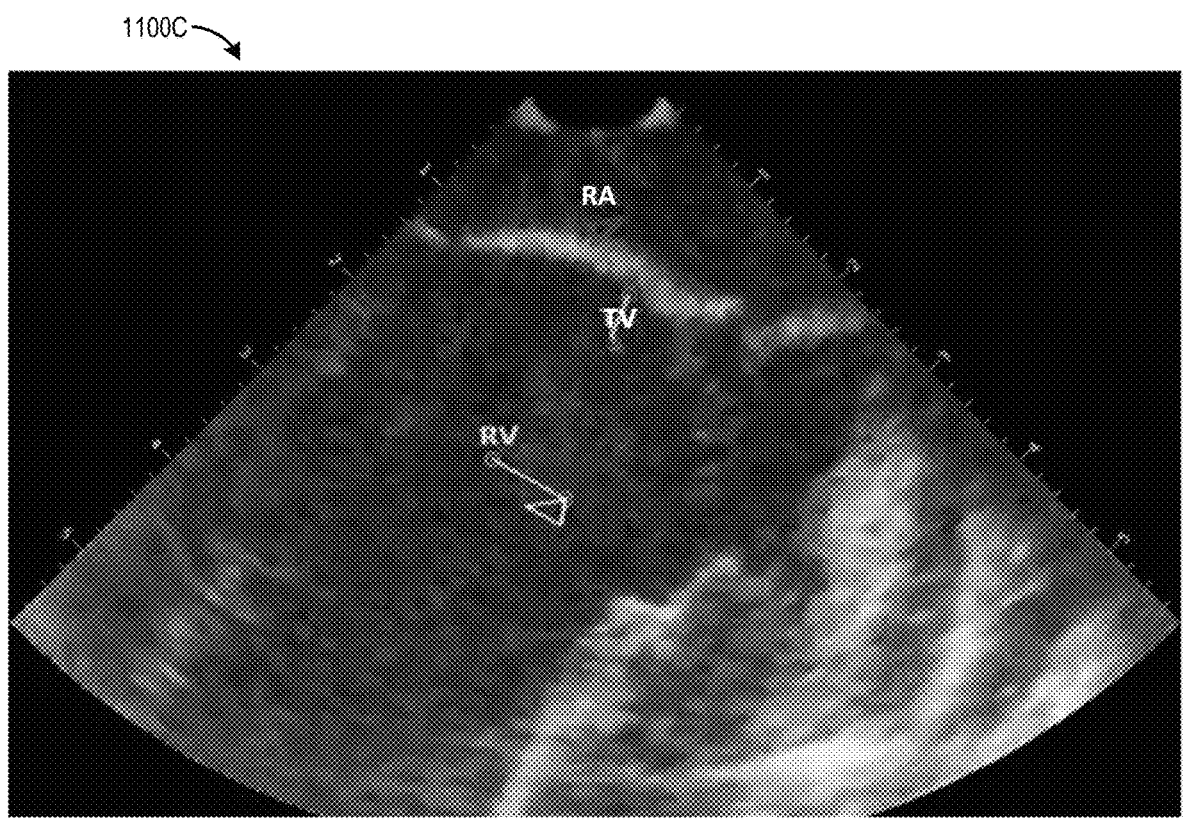

FIGS. 11A-11C depict example object/feature identification graphical user interfaces. In FIG. 11A, a graphical user interface 1100A of the Bayesian prediction system 104 is shown. The graphical user interface 1100A includes an ICE image with labels (here an "RA" and a "TV" indicator). As described herein, the Bayesian prediction system 104 can determine and validate the right atrium (RA) and tricuspid valve (TV) with Bayesian techniques. As shown, the Bayesian prediction system 104 identified the right atrium (RA) and the tricuspid valve (TV), but for whatever reason (possibly lack of training data and/or noise in the image) is unable to identify the right ventricle that lies below the TV, if RA is also seen above it.

In FIG. 11B, the graphical user interface 1100B of the Bayesian prediction system 104 can dynamically update. As described herein, the system can use a Bayesian hypothesis that has an anatomical reference and possibly additional information, as described herein, and determine that the right ventricle (RV) probably lies below the RA and TV identifications. Over a few successive frames the Bayesian prediction system 104 can increase its hypothesis to a higher confidence level, and once an acceptance threshold is satisfied, display the RV label in the graphical user interface 1100B, as shown in FIG. 11B.

In FIG. 11C, the graphical user interface 1100C can further dynamically update. As shown in FIG. 11C, the type of temporal spatial uncertainty in feature centroid location that may occur from frame to frame as a result of low-level AI object detection on per frame basis can be based at least in part on (i) expected periodic movement and/or (ii) multivariate Gaussian uncertainty attributable to multitude of reasons from training quality to live image quality to other unknown factors. The Bayesian prediction system 104 can create a confidence hypothesis, update the hypothesis based at least in part on the live data and the modified internal probability distribution assumptions, and produce results based on confidence levels of both feature/object identification and their locations, as described herein.

The graphical user interface of the Bayesian prediction system 104 can present ICE images and information on where predicted anatomical features may lie in 2D or 3D (depending on whichever ICE imaging mode is being used). A significant benefit can lie in the ability to predict where in space the out-of-frame features lie, as performed by the anatomical map based Bayesian predictor described herein.

A user may at this point request navigation aid, via the graphical user interface, to a desired location. The Bayesian prediction system 104 can have information regarding (predicted) relative spatial coordinates of out-of-frame features, as long as they're deemed to have satisfied the confidence threshold of both feature/object presence and its spatial coordinates. A user can submit a navigational request via the graphical user interface. As described herein, the graphical user interface can present an anatomical model of the heart and the user can request navigational assistance by selecting an object or feature in the presented anatomical model. Additionally or alternatively, the graphical user interface can present object/feature options (such as "right atrium (RA)," "tricuspid valve (TV)," etc.) and the graphical user interface can present navigational assistance towards a selected object/feature option. The graphical user interface can provide a navigational guide in two or three dimensions and/or in a multi-planar view equivalent of 3D imaging to guide the user to the out-of-frame object/feature(s) of interest.

Figure 12A:
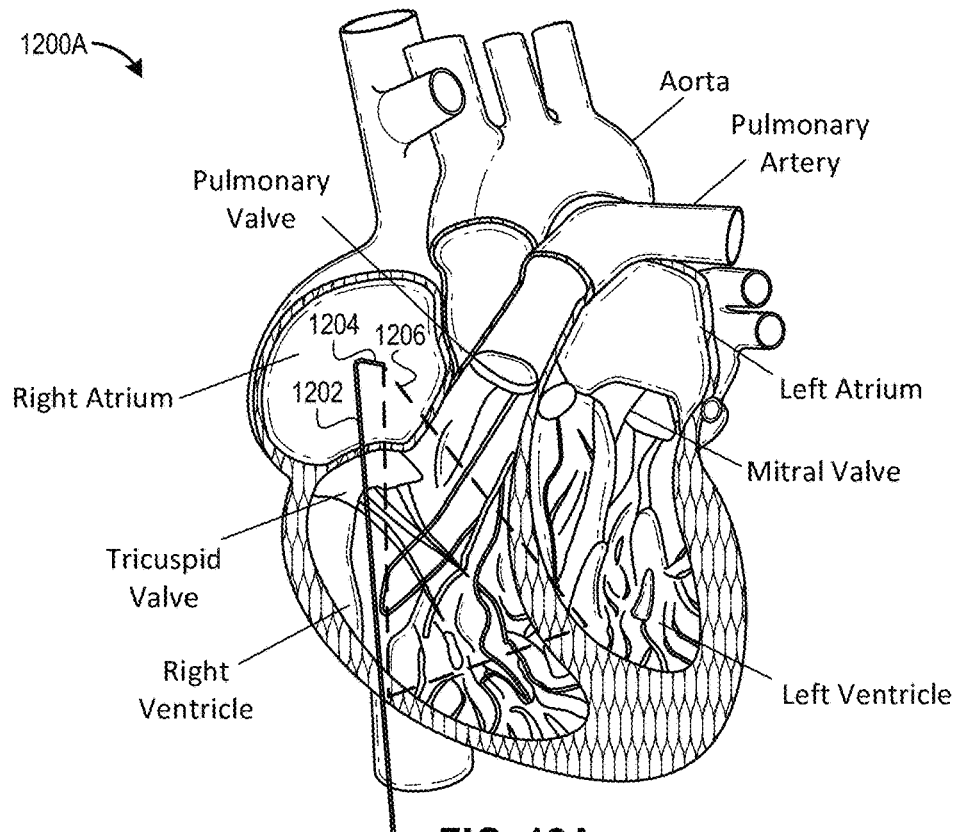
FIGS. 12A-12C depict examples of schematic diagrams of a heart with a catheter during a procedure.
Figure 12B:
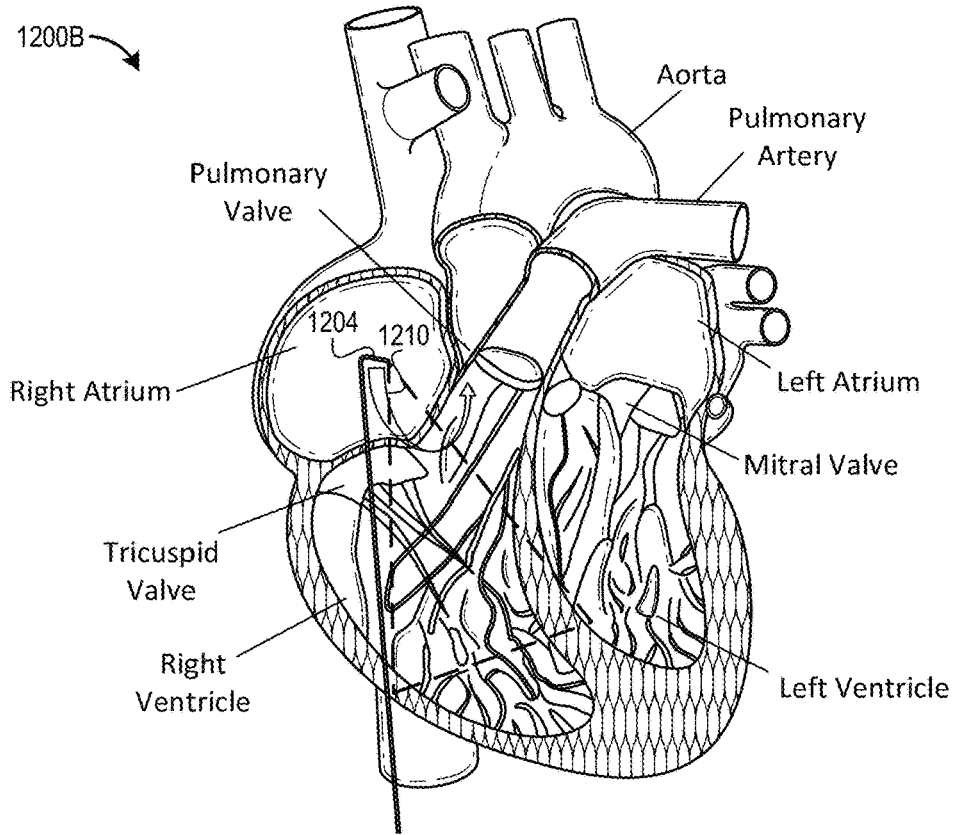
Figure 12C:
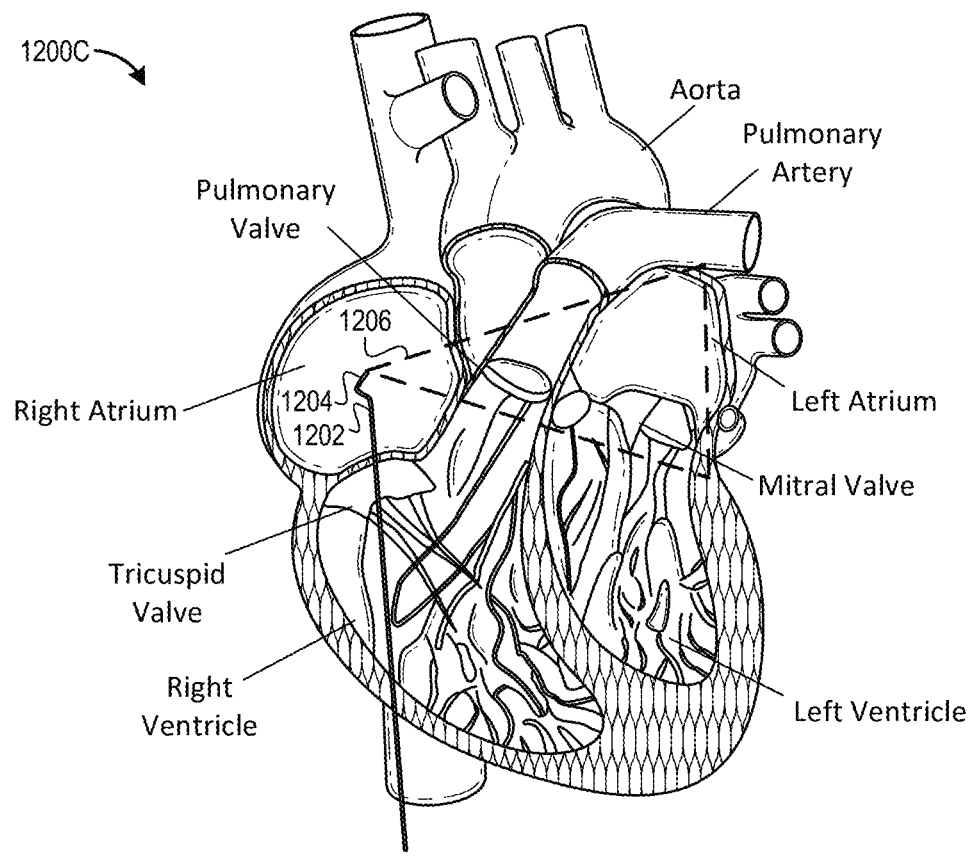

FIGS. 12A-12C depict schematic diagrams of a heart 1200A, 1200B, 1200C with an ICE catheter 1202 during a procedure. In FIG. 12A, a schematic diagram of a heart 1200A is shown in which an ICE catheter 1202 and ICE imaging tip 1204 is in an imaging position where the ICE imaging tip 1204 is in the right atrium. As shown, the field of view 1206 of the ICE imaging tip 1204 may only include the right atrium, half of the right ventricle, and part of the tricuspid valve.

In FIG. 12B, another schematic diagram of the heart 1200B, which can include a navigational element 1210, is shown. As described herein, if the user now wants to look at the left atrium and the interatrial septum (IAS), then the Bayesian prediction system 104, based at least in part on its Bayesian predictions overlaying results from the AI object detector 122, can present the navigational element 1210 within a graphical user interface. The interatrial septum is the thin wall of tissue that separates the right and left atria of the heart. In some embodiments, the navigational element 1210 can be a guide arrow. In particular, the Bayesian prediction system 104 can guide the user to the left atrium (LA) via on-screen prompts (such as the navigational element 1210) to rotate the ICE imaging tip 1204 in a direction favorable to acquiring the desired image, by utilizing its anatomical model as a map, as shown in FIG. 12B.

In FIG. 12C, another schematic diagram of the heart 1200C is shown. As shown, the user can be directed to position the ICE imaging tip 1204, which can change the field of view 1206. In some embodiments, the Bayesian prediction system 104 can receive user input from the user to request to enter the left atrium via the interatrial septum. Accordingly, the Bayesian prediction system 104 can prompt the user with navigational elements via the graphical user interface. As the user navigates according to the displayed prompts, the user can cause the catheter to end up in the left atrium via the interatrial septum.

Figure 13:
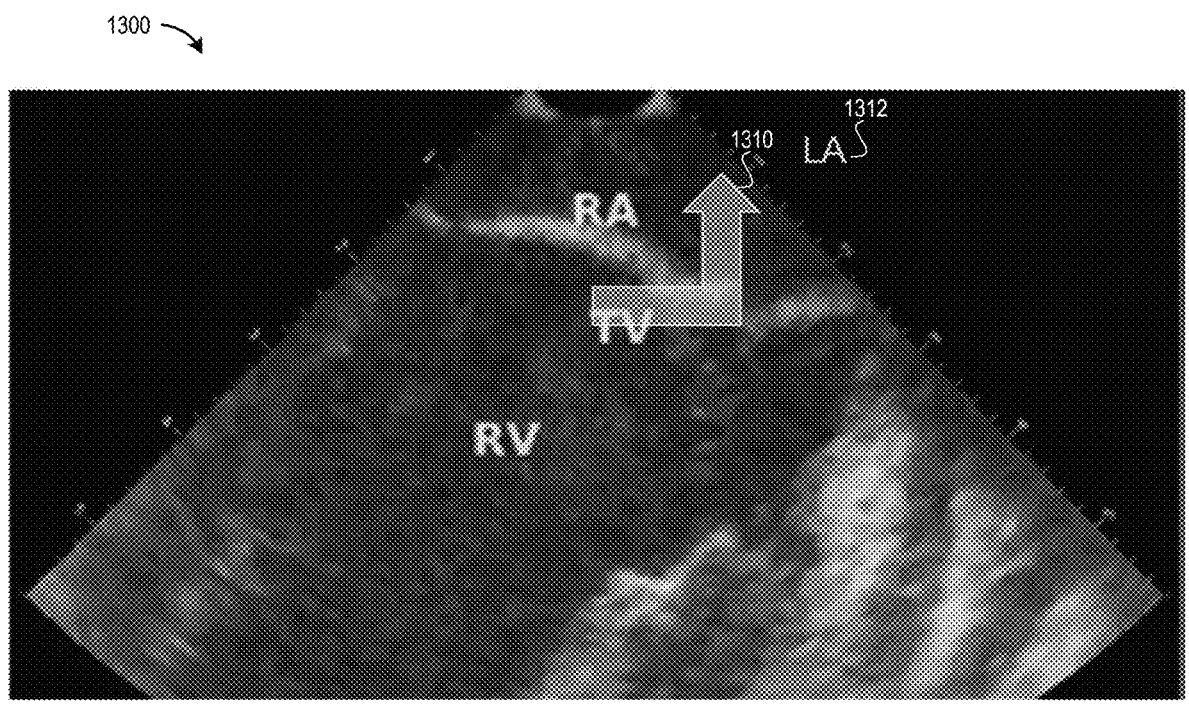
FIG. 13 depicts an example of an object/feature identification graphical user interface with a navigational element.

FIG. 13 depicts an object/feature identification graphical user interface 1300 with a navigational element 1310. The graphical user interface 1300 of FIG. 13 can be similar to the graphical user interfaces described herein, such as with respect to FIGS. 12A, 12B. The graphical user interface 1300 of FIG. 13 can include a navigational element 1310 and a label 1312 for an out-of-frame object/feature (here the left atrium (LA)). The graphical user interface 1300 of FIG. 13 can depict a state similar to the state described herein with respect to FIG. 12B. As shown, the ICE imaging tip can be oriented in the right atrium such that tricuspid valve (TV) and right ventricle (RV) and a portion of the right atrium (RA) are in view of the ICE image in the graphical user interface 1300. As described herein, the Bayesian prediction system 104 can receive user input from the user to request to look at the left atrium and the interatrial septum and/or enter the left atrium via the interatrial septum. Accordingly, the Bayesian prediction system 104 can cause the graphical user interface 1300 to present the navigational element 1310 to prompt the user to rotate the ICE catheter. As shown, the graphical user interface 1300 can also overlay the label 1312 for an out-of-frame object/feature onto the ICE image.

Figure 14:
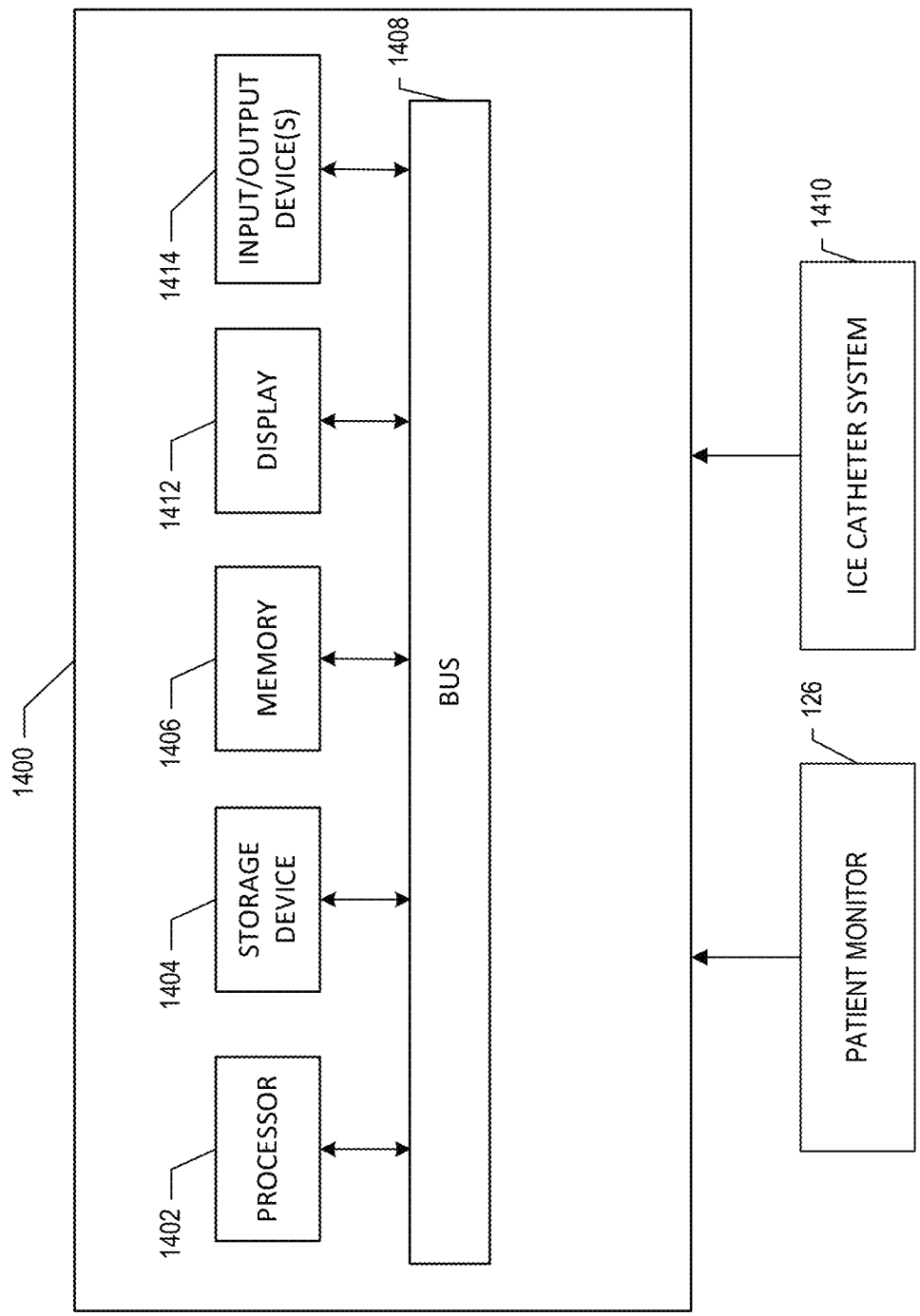
FIG. 14 is a block diagram illustrating an example computing system with which various methods and systems discussed herein may be implemented.

FIG. 14 is a block diagram that illustrates example components of a computing system 1400. The computing system 1400 can implement aspects of the present disclosure. The computing system 1400 can receive data, such as ICE images and catheter-tip embedded multi-DOF sensor data, from an ICE catheter system 1410. The computing system 1400 can vitals data (which can include ECG or blood pressure data) from the patient monitor 126.

The computing system 1400 can include a hardware processor 1402, a data storage device 1404, a memory device 1406, a bus 1408, a display 1412, and one or more input/output devices 1414. The hardware processor 1402 can also be implemented as a combination of computing devices, e.g., a combination of a digital signal processor and a microprocessor, a plurality of microprocessors, one or more microprocessors in conjunction with a digital signal processor, or any other such configuration. The hardware processor 1402 can be configured, among other things, to execute instructions to perform one or more functions. The data storage device 1404 can include a magnetic disk, optical disk, solid state drive, or flash drive, etc., and is provided and coupled to the bus 1408 for storing information and computer-executable instructions. The data storage device 1404 may be embodied in hard disk drives, solid state memories, or any other type of non-transitory computer readable storage medium. The memory device 1406 can include one or more memory devices that store data, such as, without limitation, random access memory (RAM) and read-only memory (ROM). The computer-executable instructions can be loaded into the memory device 1406. The computing system 1400 may be coupled via the bus 1408 to the display 1412, such as an LCD display or touch screen, for displaying information to a user, such as a clinician. The computing system 1400 may be coupled via the bus 1408 to one or more input/output devices 1414. The input device 1414 can include, but is not limited to, a keyboard, mouse, digital pen, microphone, or touch screen.

An AI application may be stored on the memory device 1406 and executed as a service by the hardware processor 1402. In some embodiments, the AI application may implement various aspects of the present disclosure.

It is to be understood that not necessarily all objects or advantages may be achieved in accordance with any particular embodiment described herein. Certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language used herein, such as, among others, "can," "might," "may," "e.g.," "for example," and the like, unless specifically stated otherwise, or otherwise understood within the context as used, is generally intended to convey that certain embodiments include, while other embodiments do not include, certain features, elements, or states. Thus, such conditional language is not generally intended to imply that features, elements or states are in any way required for one or more embodiments.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Such disjunctive language is not generally intended to, and should not, imply that certain embodiments require at least one of X, at least one of Y, and at least one of Z to each be present. Thus, the term "or" is used in its inclusive sense (and not in its exclusive sense) so that when used, for example, to connect a list of elements, the term "or" means one, some, or all of the elements in the list.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The terms "comprising," "including," "having," and the like are synonymous and are used inclusively, in an open-ended fashion, and do not exclude additional elements, features, acts, operations, and so forth.

The term "substantially" when used in conjunction with the term "real time" can refer to speeds in which no or little delay occurs. Substantially in real time can be associated with a threshold latency requirement that can depend on the specific implementation. In some embodiments, latency under 1 second, 500 milliseconds, 250 milliseconds, or 100 milliseconds can be substantially in real time depending on the specific context.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others.

What is claimed is:

1. A system comprising:
   an intracardiac echocardiography catheter device;
   a non-transitory data storage medium; and
   one or more computer hardware processors in communication with the non-transitory data storage medium, wherein the one or more computer hardware processors are configured to execute computer-executable instructions to at least:
      receive a first set of prior distributions;
      receive a first intracardiac echocardiography image of a subject based at least in part on data from the intracardiac echocardiography catheter device;
      receive, from an object detector, (i) a first predicted feature or object identified in the first intracardiac echocardiography image and (ii) a first location of the first predicted feature or object relative to the first intracardiac echocardiography image;
      determine a first set of posterior predictions from at least (i) a Bayesian method, (ii) the first set of prior distributions, (iii) the first intracardiac echocardiography image, (iv) the first predicted feature or object, and (v) the first location of the first predicted feature or object, wherein a first posterior prediction from the first set of posterior predictions indicates a first probability distribution associated with the first predicted feature or object;
      determine that the first probability distribution satisfies a first threshold;
      display, in a graphical user interface, (i) a first name for the first predicted feature or object associated with the first location and (ii) the first intracardiac echocardiography image;
      assign the first set of posterior predictions as a second set of prior distributions;
      receive a second intracardiac echocardiography image based at least in part on second data from the intracardiac echocardiography catheter device;
      receive, from the object detector, (i) a second predicted feature or object identified in the second intracardiac echocardiography image and (ii) a second location of the second predicted feature or object relative to the second intracardiac echocardiography image;
      determine a second set of posterior predictions from at least (i) the Bayesian method, (ii) the second set of prior distributions, (iii) the second intracardiac echocardiography image, (iv) the second predicted feature or object, and (v) the second location of the first predicted feature or object, wherein a second posterior prediction from the second set of posterior predictions indicates a second probability distribution associated with the second predicted feature or object;
      determine that the second probability distribution fails to satisfy a second threshold; and
      initiate a reset state, wherein initiating the reset state comprises resetting a set of prior distributions.

2. The system of claim 1, wherein the first set of prior distributions comprises a first prior distribution, wherein the one or more computer hardware processors is configured to execute further computer-executable instructions to at least:

determine the first prior distribution from at least one of a synthetic volumetric model of a heart, cardiac computed tomography volumetric data of another subject, or cardiac computed tomography volumetric data of the subject.

3. The system of claim 1, wherein the one or more computer hardware processors is configured to execute further computer-executable instructions to at least:
receive an anatomical model,
wherein the first set of posterior predictions is further determined from at least the anatomical model, and
wherein a second posterior prediction from the first set of posterior predictions indicates a second probability distribution associated with (i) a second predicted feature or object not identified in the first intracardiac echocardiography image and (ii) a second location of the second predicted feature or object relative to the first intracardiac echocardiography image;
determine that the second probability distribution satisfies a second threshold; and
display, in the graphical user interface, a second label name for the second predicted feature or object associated with the second location, wherein the second location is outside of the first intracardiac echocardiography image.

4. The system of claim 1, wherein the one or more computer hardware processors is configured to execute further computer-executable instructions to at least:
assign a first location and a first orientation to a device object in an anatomical model;
receive, via the graphical user interface, user input that indicates a target location within the anatomical model;
determine a navigational element from the first location, the first orientation, and the target location; and
display, in a graphical user interface, the navigational element and a second intracardiac echocardiography image.

5. The system of claim 1, wherein resetting the set of prior distributions comprises:
assigning a prior distribution to a last prior distribution that satisfied a threshold.

6. The system of claim 1, wherein the one or more computer hardware processors is configured to execute further computer-executable instructions to at least:
determine a Markov chain comprising a first state corresponding to the first predicted feature or object and a second state corresponding to an out-of-frame predicted feature or object, wherein determining the first set of posterior predictions further comprises feeding the Markov chain into the Bayesian method.

7. A system comprising:
an intracardiac echocardiography catheter device;
a non-transitory data storage medium; and
one or more computer hardware processors in communication with the non-transitory data storage medium, wherein the one or more computer hardware processors are configured to execute computer-executable instructions to at least:
receive a first set of prior distributions;
receive a first intracardiac echocardiography image of a subject based at least in part on first data from the intracardiac echocardiography catheter device;
receive, from an object detector, (i) a first predicted feature or object identified in the first intracardiac echocardiography image and (ii) a first location of the first predicted feature or object relative to the first intracardiac echocardiography image;
determine a first set of posterior predictions from at least (i) a Bayesian method, (ii) the first set of prior distributions, (iii) the first intracardiac echocardiography image, (iv) the first predicted feature or object, and (v) the first location of the first predicted feature or object, wherein a first posterior prediction from the first set of posterior predictions indicates a first probability distribution associated with the first predicted feature or object;
determine that the first probability distribution fails to satisfy a first threshold;
initiate a reset state, wherein initiating the reset state comprises resetting a second set of prior distributions instead of using the first set of posterior predictions as prior distributions;
receive a second intracardiac echocardiography image of the subject based at least in part on second data from the intracardiac echocardiography catheter device;
receive, from the object detector, (i) a second predicted feature or object identified in the second intracardiac echocardiography image and (ii) a second location of the second predicted feature or object relative to the second intracardiac echocardiography image;
determine a second set of posterior predictions from at least (i) the Bayesian method, (ii) the second set of prior distributions, (iii) the second intracardiac echocardiography image, (iv) the second predicted feature or object, and (v) the second location of the first predicted feature or object, wherein a second posterior prediction from the second set of posterior predictions indicates a second probability distribution associated with the second predicted feature or object;
determine that the second probability distribution satisfies a second threshold; and
display, in a graphical user interface, (i) a first name for the second predicted feature or object associated with the second location and (ii) the second intracardiac echocardiography image.

8. The system of claim 7, wherein the one or more computer hardware processors is configured to execute further computer-executable instructions to at least:
determine a Markov chain comprising a first state corresponding to the first predicted feature or object and a second state, wherein determining the second set of posterior predictions further comprises feeding the Markov chain into the Bayesian method.

9. The system of claim 8, wherein the one or more computer hardware processors is configured to execute further computer-executable instructions to at least:
receive vitals data for the subject; and
determine, from the vitals data, a cardiac cycle, wherein the second state corresponds to the cardiac cycle.

10. The system of claim 8, wherein the one or more computer hardware processors is configured to execute further computer-executable instructions to at least:
receive degrees of freedom sensor data associated with the intracardiac echocardiography catheter device; and
determine an orientation from the degrees of freedom sensor data, wherein the second state corresponds to the orientation.

11. The system of claim 7, wherein determining the second set of posterior predictions further comprises applying a Markov chain Monte Carlo method.

12. The system of claim 7, wherein the one or more computer hardware processors is configured to execute further computer-executable instructions to at least:
receive an anatomical model,
wherein the second set of posterior predictions is further determined from at least the anatomical model, and
wherein a third posterior prediction from the second set of posterior predictions indicates a third probability distribution associated with (i) a third predicted feature or object not identified in the second intracardiac echocardiography image and (ii) a third location of the third predicted feature or object relative to the second intracardiac echocardiography image;
determine that the third probability distribution satisfies a third threshold; and
display, in the graphical user interface, a third name for the third predicted feature or object associated with the third location, wherein the third location is outside of the second intracardiac echocardiography image.

13. The system of claim 7, wherein the one or more computer hardware processors is configured to execute further computer-executable instructions to at least:
assign a first location and a first orientation to a device object in an anatomical model;
receive, via the graphical user interface, user input that indicates a target location within the anatomical model;
determine a navigational element from the first location, the first orientation, and the target location; and
display, in a graphical user interface, the navigational element and a third intracardiac echocardiography image.

14. A method comprising:
receiving a first set of prior distributions;
receiving a first intracardiac echocardiography image of a subject based at least in part on data from an intracardiac echocardiography catheter device;
receiving, from an object detector, (i) a first predicted feature or object identified in the first intracardiac echocardiography image and (ii) a first location of the first predicted feature or object relative to the first intracardiac echocardiography image;
determining a first set of posterior predictions from at least (i) a Bayesian method, (ii) the first set of prior distributions, (iii) the first intracardiac echocardiography image, (iv) the first predicted feature or object, and (v) the first location of the first predicted feature or object, wherein a first posterior prediction from the first set of posterior predictions indicates a first probability distribution associated with the first predicted feature or object;
determining that the first probability distribution satisfies a first threshold;
displaying, in a graphical user interface, (i) a first label name for the first predicted feature or object associated with the first location and (ii) the first intracardiac echocardiography image;
assigning the first set of posterior predictions as a second set of prior distributions;
receiving a second intracardiac echocardiography image based at least in part on second data from the intracardiac echocardiography catheter device;
receiving, from the object detector, (i) a second predicted feature or object identified in the second intracardiac echocardiography image and (ii) a second location of the second predicted feature or object relative to the second intracardiac echocardiography image;
determining a second set of posterior predictions from at least (i) the Bayesian method, (ii) the second set of prior distributions, (iii) the second intracardiac echocardiography image, (iv) the second predicted feature or object, and (v) the second location of the first predicted feature or object, wherein a second posterior prediction from the second set of posterior predictions indicates a second probability distribution associated with the second predicted feature or object;
determining that the second probability distribution fails to satisfy a first threshold; and
initiating a reset state, wherein initiating the reset state comprises resetting a set of prior distributions.

15. The method of claim 14, further comprising:
receiving an anatomical model,
wherein the first set of posterior predictions is further determined from at least the anatomical model, and
wherein a second posterior prediction from the first set of posterior predictions indicates a second probability distribution associated with (i) a second predicted feature or object not identified in the first intracardiac echocardiography image and (ii) a second location of the second predicted feature or object relative to the first intracardiac echocardiography image;
determining that the second probability distribution satisfies a second threshold; and
displaying, in the graphical user interface, a second name for the second predicted feature or object associated with the second location, wherein the second location is outside of the first intracardiac echocardiography image.

16. The method of claim 14, further comprising:
assigning a first location and a first orientation to a device object in an anatomical model;
receiving, via the graphical user interface, user input that indicates a target location within the anatomical model;
determining a navigational element from the first location, the first orientation, and the target location; and
displaying, in a graphical user interface, the navigational element and a second intracardiac echocardiography image.

17. The method of claim 14, further comprising:
determining a Markov chain comprising a first state corresponding to the first predicted feature or object and a second state corresponding to an out-of-frame predicted feature or object, wherein determining the first set of posterior predictions further comprises feeding the Markov chain into the Bayesian method.

18. The method of claim 17, further comprising:
receiving vitals data; and
determining, from the vitals data, a cardiac cycle, wherein the second state corresponds to the cardiac cycle.

19. The method of claim 17, further comprising:
receiving degrees of freedom sensor data associated with the intracardiac echocardiography catheter device; and
determining an orientation from the degrees of freedom sensor data, wherein the second state corresponds to the orientation.

* * * * *